US006867291B1

(12) United States Patent
Turner, Jr. et al.

(10) Patent No.: US 6,867,291 B1
(45) Date of Patent: Mar. 15, 2005

(54) HUMAN HEMICENTIN PROTEINS AND POLYNUCLEOTIDES ENCODING THE SAME

(75) Inventors: C. Alexander Turner, Jr., The Woodlands, TX (US); Brian Mathur, The Woodlands, TX (US); Gregory Donoho, Portage, MI (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 94 days.

(21) Appl. No.: 09/953,096

(22) Filed: Sep. 14, 2001

Related U.S. Application Data

(60) Provisional application No. 60/232,793, filed on Sep. 15, 2000.

(51) Int. Cl.[7] ................................................ C07H 21/04

(52) U.S. Cl. ..................... 536/23.2; 536/23.2; 536/23.5; 530/300; 530/324; 530/333; 530/350; 530/387.1; 530/387.9; 530/388.15

(58) Field of Search ............................... 536/23.2, 23.5; 530/300, 324, 333, 350, 387.1, 387.9, 388.15

(56) References Cited

PUBLICATIONS

Bork P., 2000. Powers and Pitfalls in Sequence Analysis: The 70% Hurdle, Genome Research 10:398–400.*

* cited by examiner

*Primary Examiner*—Bruce R. Campell
*Assistant Examiner*—B. Dell Chism

(57) ABSTRACT

Novel human polynucleotide and polypeptide sequences are disclosed that can be used in therapeutic, diagnostic, and pharmacogenomic applications.

8 Claims, No Drawings

HUMAN HEMICENTIN PROTEINS AND POLYNUCLEOTIDES ENCODING THE SAME

The present application claims the benefit of U.S. Provisional Application No. 60/232,793, which was filed on Sep. 15, 2000 and is herein incorporated by reference in its entirety.

1. INTRODUCTION

The present invention relates to the discovery, identification, and characterization of novel human polynucleotides encoding proteins that share sequence similarity with mammalian membrane proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed genes, antagonists and agonists of the proteins, and other compounds that modulate the expression or activity of the proteins encoded by the disclosed genes that can be used for diagnosis, drug screening, clinical trial monitoring, the treatment of diseases and disorders, and cosmetic or nutriceutical applications.

2. BACKGROUND OF THE INVENTION

In addition to providing the structural and mechanical scaffolding for cells and tissues, proteins can also serve as recognition markers, mediate signal transduction, and can mediate or facilitate the passage of materials across the lipid bilayer. As such, proteins, and particularly protein ligands and membrane receptor proteins, are good drug targets and soluble formulations thereof can directly serve as therapeutic agents.

3. SUMMARY OF THE INVENTION

The present invention relates to the discovery, identification, and characterization of nucleotides that encode novel human hemicentin proteins, and the corresponding amino acid sequences of these proteins. The novel human proteins (NHPs) described for the first time herein share structural similarity with variety of mammalian proteins such as hemicentins, titin, basement membrane proteins, semaphorins, fibulin, and cell adhesion proteins.

The novel human nucleic acid sequences described herein encode alternative proteins/open reading frames (ORFs) of 5,518 and 4,126 amino acids in length (SEQ ID NOS: 2 and 4).

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and open reading frame or regulatory sequence replacement constructs) or to enhance the expression of the described NHPs (e.g., expression constructs that place the described polynucleotide under the control of a strong promoter system), and transgenic animals that express a NHP sequence, or "knock-out" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–4 are "knocked-out" they provide a method of identifying phenotypic expression of the particular gene as well as a method of assigning function to previously unknown genes. In addition, animals in which the unique NHP sequences described in SEQ ID NOS:1–4 are "knocked-out" provide a unique source in which to elicit antibodies to homologous and orthologous proteins-that would have been previously viewed by the immune system as "self" and therefore would have failed to elicit significant antibody responses. To these ends, gene trapped knockout ES cells have been generated in murine homologs of the described NHPs.

Additionally, the unique NHP sequences described in SEQ ID NOS:1–4 are useful for the identification of protein coding sequence and mapping a unique gene to a particular chromosome. These sequences identify actual, biologically relevant, exon splice junctions as opposed to those that might have been predicted bioinformatically from genomic sequence alone.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of the described NHP ORFs that encode the described NHP amino acid sequences.

5. DETAILED DESCRIPTION OF THE INVENTION

The NHPs described for the first time herein are novel proteins that may be expressed in, inter alia, human cell lines, fetal brain, spinal cord, thymus, pituitary, lymph node, trachea, kidney, liver, prostate, testis, stomach, small intestine, skeletal muscle, adrenal gland, heart, uterus, mammary gland, adipose, skin, esophagus, bladder, cervix, rectum, pericardium, ovary, and gene trapped human cells.

The present invention encompasses the nucleotides presented in the Sequence Listing, host cells expressing such nucleotides, the expression products of such nucleotides, and: (a) nucleotides that encode mammalian homologs of the described genes, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes:

(a) the human DNA sequences presented in the Sequence Listing (and vectors comprising the same) and additionally contemplates any nucleotide sequence encoding a contiguous HP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent expression product. Additionally contemplated are any nucleotide sequences that hybridize to the complement of a DNA sequence that encodes and expresses an amino acid sequence presented in the Sequence Listing under moderately stringent conditions, e.g., washing in 0.2×SSC/0.01% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–4 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–4, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–4 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–4.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID-NOS:1–4 provides detailed information about transcriptional changes involved in a specific pathway, potentially leading to the identification of novel components or gene functions that manifest themselves as novel phenotypes.

Probes consisting of sequences first disclosed in SEQ ID NOS:1–4 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–4 can be utilized in microarrays or other assay formats, to screen collections of genetic material from patients who have a particular medical condition. These investigations can also be carried out using the sequences first disclosed in SEQ ID NOS:1–4 in silico and by comparing previously collected genetic databases and the disclosed sequences using computer software known to those in the art.

Thus the sequences first disclosed in SEQ ID NOS:1–4 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–4. Alternatively, a restriction map specifying the relative positions of restriction endonuclease digestion sites, or various palindromic or other specific oligonucleotide sequences can be used to structurally describe a given sequence. Such restriction maps, which are typically-generated by widely available computer programs (e.g., the University of Wisconsin GCG sequence analysis package, SEQUENCHER 3.0, Gene Codes Corp., Ann Arbor, Mich., etc.), can optionally be use in conjunction with one or more discrete nucleotide sequence(s) present in the sequence that can be described by the relative position of the sequence relative to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences).

With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety that is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, cDNA obtained by reverse transcription of mRNA prepared from or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP sequence can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal sequence. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, osteoporosis, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor.) Additionally, screening can be accomplished by screening with labeled NHP fusion proteins, such as, for example, alkaline phosphatase-NHP or NHP-alkaline phosphatase fusion proteins. In cases where a NHP mutation results in an expression product with altered function (e.g., as a result of a missense or a frameshift mutation), polyclonal antibodies to NHP are likely to cross-react with a corresponding mutant NHP expression product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculovirus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP sequence under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs: that inhibit expression of a NHP sequence (transcription factor inhibitors, antisense and ribozyme molecules, or open reading frame sequence or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo;

these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 The Nhp Sequences

The cDNA sequences and the corresponding deduced amino acid sequences of the described NHPs are presented in the sequence Listing. The NHP nucleotides were obtained from clustered genomic sequence, ESTs, gene trapped sequence data, and cDNAs from mammary gland, thyroid, adipose, lymph node, testis, skeletal muscle, kidney, esophagus, heart, placenta, and bone marrow mRNAs (Edge Biosystems, Gaithersburg, Md.).

A number of polymorphism were identified during the sequencing of the NHPs that can result in a ser or pro being present at the amino acid (aa) position represented by, for example, position 133 of SEQ ID NO:2, and ile or asn at aa position 375, a lys or arg at aa position 691, a pro or leu at aa position 838, a ser or pro at aa position 1,082, a thr or ala at aa position 1,263, an asp or ala at aa position 1,556, a val or ala at aa position 2,245, a ile or thr at aa position 2,418, and a ser or thr at aa position 4,046. The present invention contemplates sequences comprising any of the above polymorphisms, as well as any and all combinations and permutations of the above.

The described NHPs are likely encoded on human chromosome 1 (see GENBANK accession no. AF156100).

An additional application of the described novel human polynucleotide sequences is their use in the molecular mutagenesis/evolution of proteins that are at least partially encoded by the described novel sequences using, for example, polynucleotide shuffling or related methodologies. Such approaches are described in U.S. Pat. Nos. 5,830,721 and 5,837,458, which are herein incorporated by reference in their entirety.

NHP gene products can also be expressed in transgenic animals. Animals of any species, including, but not limited to, worms, mice, rats, rabbits, guinea pigs, pigs, micro-pigs, birds, goats, and non-human primates, e.g., baboons, monkeys, and chimpanzees may be used to generate NHP transgenic animals.

Any technique known in the art may be used to introduce a NHP transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the NHP transgene in all their cells, as well as animals that carry the transgene in some, but not all their cells, i.e., mosaic animals or somatic cell transgenic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al., 1992, Proc. Natl. Acad. Sci. USA 89:6232–6236. The regulatory sequences required for such a cell-type specific activation will depend upon the particular cell type of interest, and will be apparent to those of skill in the art.

When it is desired that a NHP transgene be integrated into the chromosomal site of the endogenous NHP gene, gene targeting is preferred. Briefly, when such a technique is to be utilized, vectors containing some nucleotide sequences homologous to the endogenous NHP gene are designed for the purpose of integrating, via homologous recombination with chromosomal sequences, into and disrupting the function of the nucleotide sequence of the endogenous NHP gene (i.e., "knockout" animals).

The transgene can also be selectively introduced into a particular cell type, thus inactivating the endogenous NHP gene in only that cell type, by following, for example, the teaching of Gu et al., 1994, Science, 265:103–106. The regulatory sequences required for such a cell-type specific inactivation will depend upon the particular cell type of interest, and will be apparent to those of skill in the art.

Once transgenic animals have been generated, the expression of the recombinant NHP gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR.

Samples of NHP gene-expressing tissue, may also be evaluated immunocytochemically using antibodies specific for the NHP transgene product.

5.2 Nhps and Nhp Polypeptides

NHPs, NHP polypeptides, NHP peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be used as pharmaceutical reagents useful in the therapeutic treatment of mental, biological, or medical disorders and disease. Given the similarity information and expression data, the described NHPs can be targeted (by drugs, oligos, antibodies, etc.,) in order to treat disease, or to therapeutically augment the efficacy of, for example, chemotherapeutic agents used in the treatment of cancer, arthritis, or as antiviral agents.

The Sequence Listing discloses the amino acid sequences encoded by the described NHP sequences. The NHPs display initiator methionines in DNA sequence contexts consistent with translation initiation sites, and a hydrophobic region at the N-terminus that may serve as a signal sequence, which indicates that the described NHPs is probably membrane-associated or secreted, or possibly cytoplasmic.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention as are-any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but that result in a silent change, thus producing a functionally equivalent expression product. Amino acid-substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited to, the E. coli expression vector pUR278 (Ruther et al., 1983, EMBO J. 2:1791), in which a NHP coding sequence may be ligated individually into the vector in frame with the lacZ coding region so-that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target expression product can be released from the GST moiety.

In an insect system, Autographa californica nuclear polyhedrosis virus (AcNPV) is used as a vector to express foreign polynucleotide sequences. The virus grows in Spodoptera frugiperda cells. A NHP coding sequence can be cloned individually into non-essential regions (for example the polyhedrin gene) of the virus and placed under control of an ACNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen that modulates the expression of the inserted sequences, or modifies and processes the expression product in the specific fashion desired. Such modifications (e.g., glycosylation) and processing (e.g., cleavage) of protein products may be important for the function of the protein. Different host cells have characteristic and specific mechanisms for the post-translational processing and modification of proteins and expression products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the expression product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines that stably express the NHP sequences described above can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci, which in turn can be cloned and expanded into cell lines. This method may advantageously be used to engineer cell lines that express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes, which can be employed in tk$^-$, hgprt$^-$ or aprt$^-$ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the sequence of interest is subcloned into a vaccinia recombination plasmid such that the sequence's open reading frame is translationally fused to an amino-terminal tag consisting of six histidine residues. Extracts from cells infected with recombinant vaccinia virus are loaded onto $Ni^{2+}$•nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in "Liposomes:A Practical Approach", New, R.R.C., ed., Oxford University Press, New York and in U.S. Pat. Nos. 4,594,595, 5,459,127, 5,948,767 and 6,110,490 and their respective disclosures, which are herein incorporated by reference in their entirety. Additionally embodied are novel protein constructs engineered in such a way that they facilitate transport of the NHP to the target site or desired organ, where they cross the cell membrane and/or the nucleus where the NHP can exert its functional activity. This goal may be achieved by coupling of the NHP to a cytokine or other ligand that provides targeting specificity, and/or to a protein transducing domain (see generally U.S. applications Ser. No. 60/111,701 and 60/056,713, both of which are herein incorporated by reference, for examples of such transducing sequences) to facilitate passage across cellular membranes and can optionally be engineered to include nuclear localization.

5.3 Antibodies to Nhp Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP expression product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, chitosan, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diphtheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures, which are herein incorporated by reference in their entirety. Also encompassed by the present invention is the use of fully humanized monoclonal antibodies as described in U.S. Pat. No. 6,150,584 and respective disclosures, which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 341:544–546) can be adapted to produce single chain antibodies against NHP expression products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include, but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB 7(5):437–444; and Nissinoff, 1991, J. Immunol. 147(8):2429–2438). For example antibodies that bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

Additionally given the high degree of relatedness of mammalian NHPs, the presently described knock-out mice (having never seen NHP, and thus never been tolerized to NHP) have a unique utility, as they can be advantageously applied to the generation of antibodies against the disclosed mammalian NHP (i.e., NHP will be immunogenic in NHP knock-out animals).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising an open reading frame encoding an amino acid sequence drawn from the group consisting of SEQ ID NO: 2 and SEQ ID NO:4.

2. An isolated nucleic acid molecule comprising a nucleotide sequence that:

(a) encodes the amino acid sequence shown in SEQ ID NO:2; and (b) hybridizes under highly stringent conditions to the nucleotide sequence of SEQ ID NO: 1 or the complement thereof.

3. An isolated nucleic acid molecule comprising a nucleotide sequence encoding the amino acid sequence shown in SEQ ID NO:2.

4. An isolated nucleic acid molecule comprising a nucleotide sequence encoding the amino acid sequence shown in SEQ ID NO:4.

5. An expression vector comprising a nucleic acid sequence of claim 2.

6. A cell comprising the expression vector of claim 5.

7. An expression vector comprising a nucleic acid sequence of claim 4.

8. A cell comprising the expression vector of claim 7.

* * * * *

SEQUENCE LISTING

<160> NUMBER OF SEQ ID NOS: 4

<210> SEQ ID NO 1
<211> LENGTH: 16557
<212> TYPE: DNA
<213> ORGANISM: homo sapiens

<400> SEQUENCE: 1

```
atgatttcct gggaagttgt ccatacagta ttcctgtttg ctcttcttta ttcttccta      60
gctcaagatg cgagccccca gtcagagatc agagctgagg aaattcccga ggggcctcc     120
acgttggctt ttgtgtttga tgtgactggt tctatgtatg atgatttagt tcaggtgatt    180
gaagggctt ccaaaatttt ggagacgtct tgaaaagac ctaaaagacc tcttttcaac      240
tttgcgttgg tgccttttcca tgatccagaa attgggccag tgacaattac cacagatccc   300
aagaaatttc aatatgaact cagagaactg tatgttcagg tggtggtga ttgcccagaa     360
atgagtattg gagctataaa aattgccttg gaaattyctc ttcctggttc tttcatctat    420
gttttcactg atgctcggtc caaagattac cggctcaccc atgaggtgct gcaacttatc    480
caacagaaac agtcacaagt cgtatttgtt ctgactggag attgtgatga caggacccat    540
attggatata agtctatga agaaattgcc tctacaagtt ctggtcaagt gttccatctg     600
gacaaaaaac aagttaatga ggtattaaaa tgggtagaag aagcagtaca ggcctccaaa    660
gttcaccttt tatccacaga tcatttggaa caggctgtaa atacttggag aattcctttt    720
gatcccagcc tgaaagaggt cactgtgtct ttgagtgggc cttctccaat gattgaaatt    780
cgcaatcctt tagggaagct gataaaaaag gatttggcc tgcatgagct attaaatatc     840
cataactctg ccaaagtagt gaatgtgaaa gagccagagg ctggaatgtg acagtgaag    900
acctcaagca gtggaaggca ctctgttcgc attactggcc tcagtactat tgatttccga    960
gctggctttt ctcgaaagcc caccctggac ttcaaaaaaa cagtcagcag accagtgcaa   1020
ggaataccta cctatgtact gctcaatact tctggaattt ccactccagc tagaatagat   1080
cttcttgaac ttttgagtat ctcaggaagt tctcttaaga ctawtcctgt taaatattac   1140
ccacatcgaa aaccttatgg catatggaat atttctgact tgtaccacc aaatgaagct    1200
ttctttctca agtaacagg ctatgataaa gatgattacc tcttccagag agtatcaagt   1260
gtttccttt ctagtattgt cccagatgct cccaaagtta cgatgcctga aaaaccccca    1320
ggatactatc tgcagccggg ccaaattccc tgctctgttg acagtctttt gcccttacc    1380
ttgagctttg tcagaaatgg agttacactt ggagtagacc agtatttgaa agaatctgcc   1440
agtgtgaact agatattgc aaaggtcact ttgtctgacg aaggtttcta tgaatgcatt    1500
gctgtcagca gtgcaggtac tggacgggca cagacatttt ttgacgtatc agagccccct   1560
ccggtcatcc aagtgcctaa caatgttaca gtcactcctg agagagagc agttttaaca    1620
tgtctcatca tcagtgcggt ggattacaat ctaacctggc agaggaatga cagagatgtc   1680
agactggcag agccagcgag aattaggacc ttggctaatc tgtcattgga gctaaagagt   1740
gtgaaattca acgatgctgg agagtatcat tgtatggttt ctagtgaagg tggatcatca   1800
gccgcttcag ttttcctcac agtgcaagaa ccacccaaag tcactgtgat gcccaagaat   1860
cagtctttca caggagggtc tgaggtctcc atcatgtgtt ctgcaacagg ttatcccaaa   1920
ccaaagattg cctggaccgt taacgatatg tttatcgtgg gttcacacag gtataggatg   1980
acctcagatg gtaccttatt tatcaaaaat gcagctccca agatgcagg gatctatggt   2040
tgcctagcaa gtaattcagc tggaacagat aracagaatt ctactctcag atacattgaa   2100
gcccctaagt tgatggtagt tcagagtgag ctcttggttg cccttgggga tataaccgtt   2160
atggaatgca aaacctctgg tattcctcca cctcaagtta atggttcaa aggagatctt   2220
gagttgaggc cctcaacatt cctcattatt gaccctctct tgggacttttt gaagattcaa   2280
```

```
gaaacacaag atctggatgc tggcgattat acctgtgtag ccatcaatga ggctggaaga     2340
gcaactggca agataactct ggatgttggc tcacctccag ttttcataca agaacctgct     2400
gatgtgtcta tggaaattgg ctcaaatgtg acattacctt gttatgttca gggttatcca     2460
gaaccaacaa tcaaatggcg aagattagac aacatgccaa ttttctcaag acyttttca     2520 gttagttcca tcagccaact aagaacagga gctctcttta ttttaaactt atgggcaagt     2580
gataaaggaa cctatatttg tgaagctgaa accagttttg gaaagatcca gtcagagaca     2640
acagtaacag tgaccggact tgttgctcca cttattggaa tcagcccttc agtggccaat     2700
gttattgaag gacagcagct tactttgccc tgtactctgt tagctggaaa tcccattcca     2760
gaacgtcggt ggattaagaa ttcagctatg ttgctccaaa atccttacat cactgtgcgc     2820
agtgatggga gcctccatat tgaaagagtt cagcttcagg atggtggtga atatacttgt     2880
gtggccagta acgttgctgg gaccaataac aaaactacct ctgtggttgt gcatgttctg     2940
ccaaccattc agcatgggca gcagatactc agtacaattg aaggcattcc agtaacttta     3000
ccatgcaaag caagtggaaa tcccaaaccg tctgtcatct ggtccaagaa aggagagctg     3060
atttcaacca gcagtgctaa gttttcagca ggagctgatg gtagtctgta tgtggtatca     3120
cctggaggag aggagagtgg ggagtatgtc tgcactgcca ccaatacagc cggctacgcc     3180
aaaaggaaag tgcagctaac agtctatgta aggcccagag tgtttggaga tcaacgagga     3240 ctgyccccagg ataagcctgt tgagatctcc gtccttgcag gggaagaggt aacacttcca     3300
tgtgaagtga agagcttacc tccacccata attacttggg ccaaagaaac ccagctcatc     3360
tcaccgttct ctccaagaca cacattcctc ccttctggtt caatgaagat cactgaaacc     3420
cgcacttcag atagtgggat gtatctttgt gttgccacaa atattgctgg gaatgtgact     3480
caggctgtca aattaaatgt ccatgttcct ccaaagatac agcgtggacc taaacatctc     3540
aaagtccaag ttggtcaaag agtggatatt ccatgtaatg ctcaagggac tcctcttcct     3600
gtaatcacct ggtccaaagg tggaagcact atgctggttg atggagagca ccatgttagc     3660
aatccagacg gaactttaag catcgaccaa gccacgccct cagatgctgg catatataca     3720
tgtgttgcta ctaacatagc aggcactgat gaaacagaga taacgctaca tgtccaagaa     3780
ccacccrcag tggaagatct agaacctcca tataacacta ctttccaaga aagagtggcc     3840
aatcaacgca ttgaatttcc atgtcctgca aaaggtaccc ctaaaccaac catcaaatgg     3900
ttacacaatg gtagagagtt gacaggcaga gagcctggca tttctatctt ggaagatggc     3960
acattgctgg ttattgcttc tgttacaccc tatgacaatg gggagtacat ctgtgtggca     4020
gtcaatgaag ctggaaccac agaaagaaaa tataacctca agtccatgt tcctccagta    4080 attaaagata agaacaagt tacaaatgtg tcggtgttgt taaatcagct gaccaatctc     4140
ttctgtgaag tggaaggcac tccatctccc atcattatgt ggtataaaga taatgtccag     4200
gtgactgaaa gcagcactat tcagactgtg aacaatggga agatactgaa gctcttcaga     4260
gccactccag aggatgcagg aagatattcc tgcaaagcaa ttaatattgc aggcacttct     4320
cagaagtact ttaacattga tgtgctagtt ccacccacca ataggtac caacttccca     4380 aatgaagtct cagttgtcct caaccgtgac gtcgcccttg aatgccaggt caaaggcact     4440
cccttttctg atattcattg gttcaaagat ggcaagcctt tatttttggg cgatcctaat     4500
gttgaacttc tagacagagg acaagtctta catttaagaa atgcacggag aaatgacaag     4560
gggcgctacc aatgtactgt gtctaatgca gctggcaaac aagccaagga tataaaactg     4620
actatctata ttccacctag tattaaagga ggaaatgtca ccacrgmcat atcagtattg     4680
```

```
atcaacagcc ttattaaact ggaatgtgaa acacggggac ttccaatgcc tgccattact    4740
tggtataagg acgggcagcc aatcatgtcc agctcacaag cactttatat tgataaagga    4800
caatatcttc atattcctcg agcacaggtc tctgattcag caacatatac gtgtcaygta    4860
gccaatgttg ctggaactgc tgaaaaatca ttccatgtgg atgtctatgt tcctccaatg    4920
attgaaggca acttggccac gcctttgaat aagcaagtag ttattgctca ttctctgaca    4980
ctggagtgca agctgctgg aaaccttct cccattctca cctggttgaa agatggtgta     5040
cctgtgaaag ctaatgacaa tatccgcata gaagctggtg ggaagaaact cgaaatcatg    5100
agtgcccaag aaattgatcg aggacagtac atatgcgtgg ctaccagtgt ggcaggagaa    5160
aaggaaatca aatatgaagt tgatgtcttg gtgccaccag ctatagaagg aggagatgaa    5220
acatcttact tcattgtgat ggttaataac ttactggagc tagattgtca tgtgacaggc    5280
tctcccccac caactatcat gtggctgaag atggccagt taattgatga aagggatgga     5340
ttcaagattt tattaaatgg acgcaaactg gttattgctc aggctcaagt gtcaaacaca    5400
ggcctttatc ggtgcatggc agcaaatact gctggagacc acaagaagga atttgaagtg    5460
actgttcatg ttcctccaac aatcaagtcc tcaggccttt ctgagagagt tgtggtaaaa    5520
tacaagcctg tcgccttgca gtgcatagcc aatgggattc caaatccttc cattacatgg    5580
ttaaaagatg accagcctgt gaacactgcc caaggaaacc ttaaaataca gtcttctggt    5640
cgagttctac aaattgccaa aaccctgttg aagatgctg gcagatacac atgtgtggct     5700
accaacgcag ctggagaaac acaacagcac attcaactgc atgttcatga accacctagt    5760
ctggaagatg ctggaaaaat gctgaatgag actgtgttgg tgagcaaccc tgtacagctg    5820
gagtgtaagg cagctggaaa tcctgtgcct gttattacat ggtacaaaga taatcgtcta    5880
ctctcaggtt ccaccagcat gactttcttg aacagaggac agatcattga tattgaaagt    5940
gcccagatct cagatgctgg catatataaa tgcgtggcca tcaactcagc tggagctaca    6000
gagttatttt acagtctgca agttcatgtg gccccatcaa tttctggcag caataacatg    6060
gtggcagtgg tggttaataa cccggtgagg ttagaatgtg aagccagagg tattcctgcc    6120
ccaagtctga cctggttgaa agatgggagt cctgtttcta gtttttctaa tggattacag    6180
gttctctctg tggtcgaat cctagcattg accagtgcac aaatcagcga cacaggaagg      6240
tacacctgcg tggcagtgaa tgctgctgga gaaaagcaaa gggacattga cctccgagta    6300
tatgttccgc aaatattat gggagaagaa cagaatgtct ctgtcctcat tagccaagct     6360
gtggaattac tatgtcaaag tgatgctatt cccccaccta ctcttacttg gttaaaagac    6420
ggccaccct tgctgaagaa accaggcctc agtatatctg aaaatagaag tgtgttaaag     6480
attgaagatg ctcaggttca agacactggt cgttacactt gtgaagcaac aaatgttgct    6540
ggaaaaacta aaaaaacta caatgtcaac atttgggtcc ccccaaatat tggtggttct     6600
gatgaactta ctcaacttac agtcattgaa gggaatctca ttagtctgtt gtgtgaatca    6660
agtggtattc cacccccaaa tctcatctgg aagaagaaag ctctccagt gctgactgat      6720
tccatggggc gagytagaat tttatctggg ggcaggcaat tacaaatttc aattgctgaa    6780
aagtctgatg cagcactcta ttcatgtgtg gcgtcgaatg ttgctgggac tgcaaagaaa    6840
gaatacaatc tgcaagttta cattagacca accataacca acagtggcag ccaccctact    6900
gaaattattg tgacccgagg gaagagtatc tccttggagt gtgaggtgca gggtattcca    6960
ccaccaacag tgacctggat gaaagatggc caccccttga tcaaggcaaa gggagtagaa    7020
```

```
atactggatg aaggtcacat ccttcagctg aagaacattc atgtatctga cacaggccgt    7080
tatgtgtgtg ttgctgtgaa tgtagcagga atgactgaca aaaaatatga cttaagtgtc    7140
catgctcctc caagcatcat aggaaaccac aggtcacctg aaaatattag tgtggtagaa    7200
aagaactcag tatctttgac ttgtgaagct tctggaattc ccctgccttc cayaacctgg    7260
ttcaaagatg ggtggcctgt cagccttagc aattctgtga ggattctttc aggaggcagg    7320
atgctacggc tgatgcagac cacaatggaa gatgctggcc aatatacttg cgttgtaagg    7380
aatgcagctg gtgaagaaag aaaaatcttt gggctttcag tattagtacc acctcatatt    7440
gtgggtgaaa atacattgga agatgtgaag gtaaaagaga acagagtgt  tacgctgact    7500
tgtgaagtga cagggaatcc agtgccagaa attacatggc acaaagatgg gcagcccctc    7560
caagaagatg aagcccatca cattatatct ggtggccgtt ttcttcaaat taccaatgtc    7620
caggtgccac acactggaag atatacatgt ttggcttcca gtccagctgg ccacaagagc    7680
aggagcttca gtcttaatgt atttgtatct cctacaattg ctggtgtagg tagtgatggc    7740
aaccctgaag atgtcactgt catccttaac agccctacat cttggtctg tgaagcttat     7800
tcatatcctc cagctaccat cacctggttt aaggatggca ctcctttaga atctaaccga    7860
aatattcgta ttcttccagg aggcagaact ctgcagatcc tcaatgcaca ggaggacaat    7920
gctggaagat actcttgtgt agccacgaat gaggctggag aaatgataaa gcactatgaa    7980
gtgaaggtgt acattccacc cataatcaat aaaggggacc tttgggggcc aggtctttcc    8040
cctaaagaag tgaagatcaa agtaaacaac actctgacct tggaatgtga agcgtatgca    8100
attccttctg cctccctcag ctggtacaag gatggacagc cccttaaatc cgatgatcat    8160
gttaatattg ctgcgaatgg acacacactt caaataaagg aggctcaaat atcagacacc    8220
ggacgatata cttgtgtagc atctaacatt gcaggtgaag atgagttgga ttttgatgtg    8280
aatattcaag ttcctccaag ttttcagaaa ctctgggaaa taggaaacat gctagatact    8340
ggcaggaatg gtgaagccaa agatgtgatc atcaacaatc ccatttctct ttactgtgag    8400
acaaatgctg ctcccctcc tacactgaca tggtacaaag atggccaccc tctgacctca    8460
agtgataaag tattgatttt gccaggaggg cgagtgttgc agattcctcg ggctaaagta    8520
gaagatgctg ggagatacac atgtgtggct gtgaatgagg ctggagaaga ttcccttcaa    8580
tatgatgtcc gtgtactcgt gccgccaatt atcaagggag caaatagtga tctccctgaa    8640
gaggtcaccg tgctggtgaa caagagtgca ctgatagagt gtttatccag tggcagccca    8700
gcaccaagga attcctggca gaaagatgga cagcccttgc tagaagatga ccatcataaa    8760
tttctatcta atggacgaat tctgcagatt ctgaatactc aaataacaga tatcggcagg    8820
tatgtgtgtg ttgctgagaa cacagctggg agtgccaaaa atattttaa cctcaatgtt    8880
catgttcctc caagtgtcat tggtcctaaa tctgaaaatc ttaccgtcgt ggtgaacaat    8940
ttcatctctt tgacctgtga ggtctctggt tttccacctc ctgacctcag ctggctcaag    9000
aatgaacagc ccatcaaact gaacacaaat actctcattg tgcctggtgg tcgaactcta    9060
cagattattc gggccaaggt atcagatggt ggtgaataca cttgtatagc tatcaatcaa    9120
gctggcgaaa gcaagaaaaa gttttccctg actgtttatg tgcccccaag cattaaagac    9180
catgacagta atctctttc tgtagttaat gtaagagagg gaacttctgt gtctttggag    9240
tgtgagtcga acgctgtgcc acctccagtc atcacttggt ataagaatgg gcggatgata    9300
acagagtcta ctcatgtgga gattttagct gatggcaaaa tgctacacat taagaaagct    9360
gaggtatctg acacaggcca gtatgtatgt agagctataa atgtagcagg acgggatgat    9420
```

```
aaaaatttcc acctcaatgt atatgtgcca cccagtattg aaggacctga aagagaagtg    9480
attgtggaga cgatcagcaa tcctgtgaca ttaacatgtg atgccactgg gatcccacct    9540
cccacgatag catggttaaa gaaccacaag cgcatagaaa attctgactc actggaagtt    9600
cgtattttgt ctggaggtag caaactccag attgcccggt ctcagcattc agatagtgga    9660
aactatacat gtattgcttc aaatatggag ggaaaagccc agaaatatta ctttctttca    9720
attcaagttc ctccaagtgt tgctggtgct gaaattccaa gtgatgtcag tgtccttcta    9780
ggagaaaatg ttgagctggt ctgcaatgca aatggcattc ctactccact tattcaatgg    9840
cttaaagatg gaaagcccat agctagtggt gaaacagaaa gaatccgagt gagtgcaaat    9900
ggcagcacat taaacattta tggagctctt acatctgaca cggggaaata cacatgtgtt    9960
gctactaatc ccgctggaga agaagaccga attttttaact tgaatgtcta tgttacacct   10020
acaattaggg gtaataaaga tgaagcagag aaactaatga ctttagtgga tacttcaata   10080
aatattgaat gcagagccac agggacgcct ccaccacaga taaactggct gaagaatgga   10140
cttcctctgc ctctctcctc ccatatccgg ttactggcag caggacaagt tatcaggatt   10200
gtgagagctc aggtgtctga tgtcgctgtg tatacttgtg tggcctccaa cagagctggg   10260
gtggataata agcattacaa tcttcaagtg tttgcaccac caaatatgga caattcaatg   10320
gggacagagg aaatcacagt tctcaaaggt agttccacct ctatggcatg cattactgat   10380
ggaaccccag ctcccagtat ggcctggctt agagatggcc agcctctggg gcttgatgcc   10440
catctgacag tcagcaccca tggaatggtc ctgcagctcc tcaaagcaga gactgaagat   10500
tcgggaaagt acacctgcat tgcctcaaat gaagctggag aagtcagcaa gcactttatc   10560
ctcaaggtcc tagaaccacc tcacattaat ggatctgaag aacatgaaga gatatcagta   10620
attgttaata cccacttgaa acttacctgc attgcttctg gaatcccagc ccctaaaatg   10680
acctggatga aagatggccg gccccttcca cagacggatc aagtgcaaac tctaggagga   10740
ggagaggttc ttcgaatttc tactgctcag gtggaggata caggaagata tacatgtctg   10800
gcatccagtc ctgcaggaga tgatgataag gaatatctag tgagagtgca tgtacctcct   10860
aatattgctg gaactgatga gccccgggat atcactgtgt tacggaacag acaagtgaca   10920
ttggaatgca gtcagatgc agtgccccca cctgtaatta cttggctcag aaatggagaa   10980
cggttacagg caacacctcg agtgcgaatc ctatctggag ggagatactt gcaaatcaac   11040
aatgctgacc taggtgatac agccaattat acctgtgttg ccagcaacat gcaggaaag   11100
actacaagag aatttattct cactgtaaat gttcctccaa acataaaggg gggcccccag   11160
agccttgtaa ttcttttaaa taagtcaact gtattggaat gcatcgctga aggtgtgcca   11220
actccaagga taacatggag aaaggatgga gctgttctag ctgggaatca tgcaagatat   11280
tccatcttgg aaaatggatt ccttcatatt caatcagcac atgtcactga cactggacgg   11340
tatttgtgta tggccaccaa tgctgctgga acagatcgca ggcgaataga tttacaggtc   11400
catgttcctc catctattgc tccgggtcct accaacatga ctgtaatagt aaatgttcaa   11460
actactctgg cttgtgaggc tactgggata ccaaaaccat caatcaattg gagaaaaaat   11520
gggcatcttc ttaatgtgga tcaaaatcag aactcataca ggctccttt ttcaggttca   11580
ctagtaatta tttccccttc tgtggatgac actgcaacct atgaatgtac tgtgacaaac   11640
ggtgctggag atgataaaag aactgtggat ctcactgtcc aagttccacc ttccatagct   11700
gatgagccta cagatttcct agtaaccaaa catgccccag cagtaattac ctgcactgct   11760
```

```
tcgggagttc catttccctc aattcactgg accaaaaatg gtataagact gcttcccagg    11820
ggagatggct atagaattct gtcctcagga gcaattgaaa tacttgccac ccaattaaac    11880
catgctggaa gatacacttg tgtcgctagg aatgcggctg gctctgcaca tcgacacgts    11940
acccttcatg ttcatgagcc tccagtcatt cagccccaac caagtgaact acacgtcatt    12000
ctgaacaatc ctattttatt accatgtgaa gcaacaggga cacccagtcc tttcattact    12060
tggcaaaaag aaggcatcaa tgttaacact tcaggcagaa accatgcagt tcttcctagt    12120
ggcggcttac agatcwccag agctgtccga gaggatgctg gcacttacat gtgtgtggcc    12180
cagaacccgg ctggtacagc cttgggcaaa atcaagttaa atgtccaagt tcctccagtc    12240
attagccctc atctaaagga atatgttatt gctgtggaca agcccatcac gttatcctgt    12300
gaagcagatg gcctccctcc gcctgacatt acatggcata agatgggcg tgcaattgtg    12360 gaatctatcc gccagcgcgt cctcagctct ggctctctgc aaatagcatt tgtccagcct    12420
ggtgatgctg gccattacac gtgcatggca gccaatgtag caggatcaag cagcacaagc    12480
accaagctca ccgtccatgt accacccagg atcagaagta cagaaggaca ctacacggtc    12540
aatgagaatt cacaagccat tcttccatgc gtagctgatg gaatccccac accagcaatt    12600
aactggaaaa aagacaatgt tcttttagct aacttgttag gaaaatacac tgctgaacca    12660 tatgagaac tcattttaga aaatgttgtg ctggaggatt ctggcttcta tacctgtgtt    12720
gctaacaatg ctgcaggtga agatacacac actgtcagcc tgactgtgca tgttctcccc    12780
acttttactg aacttcctgg agacgtgtca ttaaataaag gagaacagct acgattaagc    12840
tgtaaagcta ctggtattcc attgcccaaa ttaacatgga ccttcaataa caatattatt    12900
ccagcccact ttgacagtgt gaatggacac agtgaacttg ttattgaaag agtgtcaaaa    12960
gaggattcag gtacttatgt gtgcaccgca gagaacagcg ttggctttgt gaaggcaatt    13020
ggatttgttt atgtgaaaga acctccagtc ttcaaaggtg attatccttc taactggatt    13080
gaaccacttg gtgggaatgc aatcctgaat tgtgaggtga aggagaccc cacccccaacc    13140 atccagtgga acagaaaggg agtggatatt gaaattagcc acagaatccg gcaactgggc    13200
aatggctccc tggccatcta tggcactgtt aatgaagatg ccggtgacta tacatgtgta    13260
gctaccaatg aagctggggt ggtggagcgc agcatgagtc tgactctgca aagtcctcct    13320
attatcactc ttgagccagt ggaaactgtt attaatgctg gtggcaaaat catattgaat    13380
tgtcaggcaa ctggagagcc tcaaccaacc attacatggt cccgtcaagg gcactctatt    13440
tcctgggatg accgggttaa cgtgttgtcc aacaactcat tatatattgc tgatgctcag    13500
aaagaagata cctctgaatt tgaatgtgtt gctcgaaact taatgggttc tgtccttgtc    13560
agagtgccag tcatagtcca ggttcatggt ggattttccc agtggtctgc atggagagcc    13620
tgcagtgtca cctgtggaaa aggcatccaa aagaggagtc gtctgtgcaa ccagccccctt    13680 ccagccaatg gtgggaagcc ctgccaaggt tcagatttgg aaatgcgaaa ctgtcaaaat    13740
aagccttgtc cagtggatgg tagctggtcg gaatggagtc tttgggaaga atgcacaagg    13800
agctgtggac gcgcaaccac aaccaggacc aggacttgca ataatccatc agttcagcat    13860
ggtgggcggc catgtgaagg gaatgctgtg gaaataatta tgtgcaacat taggccttgc    13920
ccagttcatg gagcatggag cgcttggcag ccttggggaa catgcagcga aagttgtggg    13980
aaaggtactc agacaagagc aagactttgt aataacccac caccagcgtt tggtgggtcc    14040
tactgtgatg gagcagaaac acagatgcaa gtttgcaatg aaagaaattg tccaattcat    14100
ggcaagtggg cgacttgggc cagttggagt gcctgttctg tgtcatgtgg aggaggtgcc    14160
```

```
agacagagaa caaggggctg ctccgaccct gtgcccagt atggaggaag gaaatgcgaa    14220
gggagtgatg tccagagtga ttttttgcaac agtgacccttt gcccaaccca tggtaactgg   14280
agtccttgga gtggctgggg aacatgcagc cggacgtgta acggagggca gatgcggcgg    14340
taccgcacat gtgataaccc tcctccctcc aatgggggaa gagcttgtgg gggaccagac    14400
tcccagatcc agaggtgcaa cactgacatg tgtcctgtgg atggaagttg gggaagctgg    14460
catagttgga gccagtgctc tgcctcctgt ggaggaggtg aaaagactcg aagcggctg     14520
tgcgaccatc ctgtgccagt taaaggtggc cgtccctgtc ccggagacac tactcaggtg    14580
accaggtgca atgtacaagc atgtccaggt gggccccagc gagccagagg aagtgttatt    14640
ggaaatatta atgatgttga atttggaatt gctttcctta atgccacaat aactgatagc    14700
cctaactctg atactagaat aatacgtgcc aaaattacca atgtacctcg tagtcttggt    14760
tcagcaatga gaaagatagt ttctattcta aatcccattt attggacaac agcaaaggaa    14820
ataggagaag cagtcaatgg ctttaccctc accaatgcag tcttcaaaag agaaactcaa    14880
gtggaatttg caactggaga aatcttgcag atgagtcata ttgcccgggg cttggattcc    14940
gatggttctt tgctgctaga tatcgttgtg agtggctatg tcctacagct tcagtcacct    15000
gctgaagtca ctgtaaagga ttacacagag gactacattc aaacaggtcc tgggcagctg    15060
tacgcctact caacccggct gttcaccatt gatggcatca gcatcccata cacatggaac    15120
cacaccgttt tctatgatca ggcacaggga agaatgcctt tcttggttga aacacttcat    15180
gcatcctctg tggaatctga ctataaccag atagaagaga cactgggttt taaaattcat    15240
gcttcaatat ccaaaggaga tcgcagtaat cagtgcccct ccgggtttac cttagactca    15300
gttgaccctt tttgtgctga tgaggatgaa tgtgcagcag ggaatccctg ctcccatagc    15360
tgccacaatg ccatggggac ttactactgc tcctgcccta aaggcctcac catagctgca    15420
gatgaagaa cttgtcaaga tattgatgag tgtgcttttgg gtaggcatac ctgccacgct    15480
ggtcaggact gtgacaatac gattggatct tatcgctgtg tggtccgttg tggaagtggc    15540
tttcgaagaa cctctgatgg gctgagttgt caagatatta atgaatgtca gaatccagc    15600
ccctgtcacc agcgctgttt caatgccata ggaagtttcc attgtggatg tgaacctggg    15660
tatcagctca aaggcagaaa atgcatggat gtgaacgagt gtagacaaaa tgtatgcaga    15720
ccagatcagc actgtaagaa cacccgtggt ggctataagt gcattgatct ttgtccaaat    15780
ggaatgacca aggcagaaaa tggaacctgt attgatattg atgaatgtaa agatgggacc    15840
catcagtgca gatataacca gatatgtgag aatacaagag gcagctatcg ttgtgtatgc    15900
ccaagaggtt atcggtctca aggagttgga agaccctgca tggatattga tgaatgtgaa    15960
aatacagatg cctgccagca tgagtgtaag aataccttg gaagttatca gtgcatctgc    16020
ccacctggct atcaactcac acacaatgga agacatgcc aagatatcga tgaatgtctg    16080
gagcagaatg tgcactgtgg acccaatcgc atgtgcttca acatgagagg aagctaccag    16140
tgcatcgata cccctgtcc acccaactac caacgggatc ctgtttcagg ttctgcctc    16200
aagaactgtc cacccaatga tttggaatgt gccttgagcc catatgcctt ggaatacaaa    16260
ctcgtctccc tcccatttgg aatagccacc aatcaagatt taatccggct ggttgcatac    16320
acacaggatg gagtgatgca tcccaggaca actttcctca tggtagatga ggaacagact    16380
gttccttttg ccttgaggga tgaaaacctg aaaggagtgg tgtatacaac acgaccacta    16440
cgagaagcag agacctaccg catgagggtc cgagcctcat cctacagtgc caatgggacc    16500
```

```
attgaatatc agaccacatt catagtttat atagctgtgt ccgcctatcc atactaa    16557
```

<210> SEQ ID NO 2
<211> LENGTH: 5518
<212> TYPE: PRT
<213> ORGANISM: homo sapiens
<220> FEATURE:
<221> NAME/KEY: VARIANT
<222> LOCATION: (1)...(5518)
<223> OTHER INFORMATION: Xaa = Any Amino Acid

<400> SEQUENCE: 2

```
Met Ile Ser Trp Glu Val Val His Thr Val Phe Leu Phe Ala Leu Leu
  1               5                  10                  15

Tyr Ser Ser Leu Ala Gln Asp Ala Ser Pro Gln Ser Glu Ile Arg Ala
             20                  25                  30

Glu Glu Ile Pro Glu Gly Ala Ser Thr Leu Ala Phe Val Phe Asp Val
         35                  40                  45

Thr Gly Ser Met Tyr Asp Asp Leu Val Gln Val Ile Glu Gly Ala Ser
     50                  55                  60

Lys Ile Leu Glu Thr Ser Leu Lys Arg Pro Lys Arg Pro Leu Phe Asn
 65                  70                  75                  80

Phe Ala Leu Val Pro Phe His Asp Pro Glu Ile Gly Pro Val Thr Ile
                 85                  90                  95

Thr Thr Asp Pro Lys Lys Phe Gln Tyr Glu Leu Arg Glu Leu Tyr Val
            100                 105                 110

Gln Gly Gly Gly Asp Cys Pro Glu Met Ser Ile Gly Ala Ile Lys Ile
        115                 120                 125

Ala Leu Glu Ile Xaa Leu Pro Gly Ser Phe Ile Tyr Val Phe Thr Asp
    130                 135                 140

Ala Arg Ser Lys Asp Tyr Arg Leu Thr His Glu Val Leu Gln Leu Ile
145                 150                 155                 160

Gln Gln Lys Gln Ser Gln Val Val Phe Val Leu Thr Gly Asp Cys Asp
                165                 170                 175

Asp Arg Thr His Ile Gly Tyr Lys Val Tyr Glu Glu Ile Ala Ser Thr
            180                 185                 190

Ser Ser Gly Gln Val Phe His Leu Asp Lys Lys Gln Val Asn Glu Val
        195                 200                 205

Leu Lys Trp Val Glu Glu Ala Val Gln Ala Ser Lys Val His Leu Leu
    210                 215                 220

Ser Thr Asp His Leu Glu Gln Ala Val Asn Thr Trp Arg Ile Pro Phe
225                 230                 235                 240

Asp Pro Ser Leu Lys Glu Val Thr Val Ser Leu Ser Gly Pro Ser Pro
                245                 250                 255

Met Ile Glu Ile Arg Asn Pro Leu Gly Lys Leu Ile Lys Lys Gly Phe
            260                 265                 270

Gly Leu His Glu Leu Leu Asn Ile His Asn Ser Ala Lys Val Val Asn
        275                 280                 285

Val Lys Glu Pro Glu Ala Gly Met Trp Thr Val Lys Thr Ser Ser Ser
    290                 295                 300

Gly Arg His Ser Val Arg Ile Thr Gly Leu Ser Thr Ile Asp Phe Arg
305                 310                 315                 320

Ala Gly Phe Ser Arg Lys Pro Thr Leu Asp Phe Lys Lys Thr Val Ser
                325                 330                 335

Arg Pro Val Gln Gly Ile Pro Thr Tyr Val Leu Leu Asn Thr Ser Gly
            340                 345                 350
```

-continued

```
Ile Ser Thr Pro Ala Arg Ile Asp Leu Leu Glu Leu Leu Ser Ile Ser
        355                 360                 365
Gly Ser Ser Leu Lys Thr Xaa Pro Val Lys Tyr Tyr Pro His Arg Lys
    370                 375                 380
Pro Tyr Gly Ile Trp Asn Ile Ser Asp Phe Val Pro Pro Asn Glu Ala
385                 390                 395                 400
Phe Phe Leu Lys Val Thr Gly Tyr Asp Lys Asp Asp Tyr Leu Phe Gln
                405                 410                 415
Arg Val Ser Ser Val Ser Phe Ser Ser Ile Val Pro Asp Ala Pro Lys
            420                 425                 430
Val Thr Met Pro Glu Lys Thr Pro Gly Tyr Tyr Leu Gln Pro Gly Gln
        435                 440                 445
Ile Pro Cys Ser Val Asp Ser Leu Leu Pro Phe Thr Leu Ser Phe Val
    450                 455                 460
Arg Asn Gly Val Thr Leu Gly Val Asp Gln Tyr Leu Lys Glu Ser Ala
465                 470                 475                 480
Ser Val Asn Leu Asp Ile Ala Lys Val Thr Leu Ser Asp Glu Gly Phe
                485                 490                 495
Tyr Glu Cys Ile Ala Val Ser Ser Ala Gly Thr Gly Arg Ala Gln Thr
            500                 505                 510
Phe Phe Asp Val Ser Glu Pro Pro Val Ile Gln Val Pro Asn Asn
        515                 520                 525
Val Thr Val Thr Pro Gly Glu Arg Ala Val Leu Thr Cys Leu Ile Ile
    530                 535                 540
Ser Ala Val Asp Tyr Asn Leu Thr Trp Gln Arg Asn Asp Arg Asp Val
545                 550                 555                 560
Arg Leu Ala Glu Pro Ala Arg Ile Arg Thr Leu Ala Asn Leu Ser Leu
                565                 570                 575
Glu Leu Lys Ser Val Lys Phe Asn Asp Ala Gly Glu Tyr His Cys Met
            580                 585                 590
Val Ser Ser Glu Gly Gly Ser Ser Ala Ala Ser Val Phe Leu Thr Val
        595                 600                 605
Gln Glu Pro Pro Lys Val Thr Val Met Pro Lys Asn Gln Ser Phe Thr
    610                 615                 620
Gly Gly Ser Glu Val Ser Ile Met Cys Ser Ala Thr Gly Tyr Pro Lys
625                 630                 635                 640
Pro Lys Ile Ala Trp Thr Val Asn Asp Met Phe Ile Val Gly Ser His
                645                 650                 655
Arg Tyr Arg Met Thr Ser Asp Gly Thr Leu Phe Ile Lys Asn Ala Ala
            660                 665                 670
Pro Lys Asp Ala Gly Ile Tyr Gly Cys Leu Ala Ser Asn Ser Ala Gly
        675                 680                 685
Thr Asp Xaa Gln Asn Ser Thr Leu Arg Tyr Ile Glu Ala Pro Lys Leu
    690                 695                 700
Met Val Val Gln Ser Glu Leu Leu Val Ala Leu Gly Asp Ile Thr Val
705                 710                 715                 720
Met Glu Cys Lys Thr Ser Gly Ile Pro Pro Pro Gln Val Lys Trp Phe
                725                 730                 735
Lys Gly Asp Leu Glu Leu Arg Pro Ser Thr Phe Leu Ile Ile Asp Pro
            740                 745                 750
Leu Leu Gly Leu Leu Lys Ile Gln Glu Thr Gln Asp Leu Asp Ala Gly
        755                 760                 765
```

-continued

```
Asp Tyr Thr Cys Val Ala Ile Asn Glu Ala Gly Arg Ala Thr Gly Lys
770                 775                 780
Ile Thr Leu Asp Val Gly Ser Pro Val Phe Ile Gln Glu Pro Ala
785                 790                 795                 800
Asp Val Ser Met Glu Ile Gly Ser Asn Val Thr Leu Pro Cys Tyr Val
                805                 810                 815
Gln Gly Tyr Pro Glu Pro Thr Ile Lys Trp Arg Arg Leu Asp Asn Met
                820                 825                 830
Pro Ile Phe Ser Arg Xaa Phe Ser Val Ser Ser Ile Ser Gln Leu Arg
                835                 840                 845
Thr Gly Ala Leu Phe Ile Leu Asn Leu Trp Ala Ser Asp Lys Gly Thr
850                 855                 860
Tyr Ile Cys Glu Ala Glu Asn Gln Phe Gly Lys Ile Gln Ser Glu Thr
865                 870                 875                 880
Thr Val Thr Val Thr Gly Leu Val Ala Pro Leu Ile Gly Ile Ser Pro
                885                 890                 895
Ser Val Ala Asn Val Ile Glu Gly Gln Gln Leu Thr Leu Pro Cys Thr
                900                 905                 910
Leu Leu Ala Gly Asn Pro Ile Pro Glu Arg Arg Trp Ile Lys Asn Ser
                915                 920                 925
Ala Met Leu Leu Gln Asn Pro Tyr Ile Thr Val Arg Ser Asp Gly Ser
930                 935                 940
Leu His Ile Glu Arg Val Gln Leu Gln Asp Gly Gly Glu Tyr Thr Cys
945                 950                 955                 960
Val Ala Ser Asn Val Ala Gly Thr Asn Asn Lys Thr Thr Ser Val Val
                965                 970                 975
Val His Val Leu Pro Thr Ile Gln His Gly Gln Gln Ile Leu Ser Thr
                980                 985                 990
Ile Glu Gly Ile Pro Val Thr Leu Pro Cys Lys Ala Ser Gly Asn Pro
            995                 1000                1005
Lys Pro Ser Val Ile Trp Ser Lys Lys Gly Glu Leu Ile Ser Thr Ser
            1010                1015                1020
Ser Ala Lys Phe Ser Ala Gly Ala Asp Gly Ser Leu Tyr Val Val Ser
1025                1030                1035                1040
Pro Gly Gly Glu Glu Ser Gly Glu Tyr Val Cys Thr Ala Thr Asn Thr
                1045                1050                1055
Ala Gly Tyr Ala Lys Arg Lys Val Gln Leu Thr Val Tyr Val Arg Pro
                1060                1065                1070
Arg Val Phe Gly Asp Gln Arg Gly Leu Xaa Gln Asp Lys Pro Val Glu
                1075                1080                1085
Ile Ser Val Leu Ala Gly Glu Glu Val Thr Leu Pro Cys Glu Val Lys
                1090                1095                1100
Ser Leu Pro Pro Pro Ile Ile Thr Trp Ala Lys Glu Thr Gln Leu Ile
1105                1110                1115                1120
Ser Pro Phe Ser Pro Arg His Thr Phe Leu Pro Ser Gly Ser Met Lys
                1125                1130                1135
Ile Thr Glu Thr Arg Thr Ser Asp Ser Gly Met Tyr Leu Cys Val Ala
                1140                1145                1150
Thr Asn Ile Ala Gly Asn Val Thr Gln Ala Val Lys Leu Asn Val His
                1155                1160                1165
Val Pro Pro Lys Ile Gln Arg Gly Pro Lys His Leu Lys Val Gln Val
                1170                1175                1180
Gly Gln Arg Val Asp Ile Pro Cys Asn Ala Gln Gly Thr Pro Leu Pro
```

-continued

```
            1185                1190                1195                1200
Val Ile Thr Trp Ser Lys Gly Gly Ser Thr Met Leu Val Asp Gly Glu
                1205                1210                1215
His His Val Ser Asn Pro Asp Gly Thr Leu Ser Ile Asp Gln Ala Thr
                1220                1225                1230
Pro Ser Asp Ala Gly Ile Tyr Thr Cys Val Ala Thr Asn Ile Ala Gly
                1235                1240                1245
Thr Asp Glu Thr Glu Ile Thr Leu His Val Gln Glu Pro Pro Xaa Val
                1250                1255                1260
Glu Asp Leu Glu Pro Pro Tyr Asn Thr Thr Phe Gln Glu Arg Val Ala
1265                1270                1275                1280
Asn Gln Arg Ile Glu Phe Pro Cys Pro Ala Lys Gly Thr Pro Lys Pro
                1285                1290                1295
Thr Ile Lys Trp Leu His Asn Gly Arg Glu Leu Thr Gly Arg Glu Pro
                1300                1305                1310
Gly Ile Ser Ile Leu Glu Asp Gly Thr Leu Leu Val Ile Ala Ser Val
                1315                1320                1325
Thr Pro Tyr Asp Asn Gly Glu Tyr Ile Cys Val Ala Val Asn Glu Ala
                1330                1335                1340
Gly Thr Thr Glu Arg Lys Tyr Asn Leu Lys Val His Val Pro Pro Val
1345                1350                1355                1360
Ile Lys Asp Lys Glu Gln Val Thr Asn Val Ser Val Leu Leu Asn Gln
                1365                1370                1375
Leu Thr Asn Leu Phe Cys Glu Val Glu Gly Thr Pro Ser Pro Ile Ile
                1380                1385                1390
Met Trp Tyr Lys Asp Asn Val Gln Val Thr Glu Ser Ser Thr Ile Gln
                1395                1400                1405
Thr Val Asn Asn Gly Lys Ile Leu Lys Leu Phe Arg Ala Thr Pro Glu
                1410                1415                1420
Asp Ala Gly Arg Tyr Ser Cys Lys Ala Ile Asn Ile Ala Gly Thr Ser
1425                1430                1435                1440
Gln Lys Tyr Phe Asn Ile Asp Val Leu Val Pro Pro Thr Ile Ile Gly
                1445                1450                1455
Thr Asn Phe Pro Asn Glu Val Ser Val Val Leu Asn Arg Asp Val Ala
                1460                1465                1470
Leu Glu Cys Gln Val Lys Gly Thr Pro Phe Pro Asp Ile His Trp Phe
                1475                1480                1485
Lys Asp Gly Lys Pro Leu Phe Leu Gly Asp Pro Asn Val Glu Leu Leu
                1490                1495                1500
Asp Arg Gly Gln Val Leu His Leu Lys Asn Ala Arg Arg Asn Asp Lys
1505                1510                1515                1520
Gly Arg Tyr Gln Cys Thr Val Ser Asn Ala Ala Gly Lys Gln Ala Lys
                1525                1530                1535
Asp Ile Lys Leu Thr Ile Tyr Ile Pro Pro Ser Ile Lys Gly Gly Asn
                1540                1545                1550
Val Thr Thr Xaa Ile Ser Val Leu Ile Asn Ser Leu Ile Lys Leu Glu
                1555                1560                1565
Cys Glu Thr Arg Gly Leu Pro Met Pro Ala Ile Thr Trp Tyr Lys Asp
                1570                1575                1580
Gly Gln Pro Ile Met Ser Ser Gln Ala Leu Tyr Ile Asp Lys Gly
1585                1590                1595                1600
Gln Tyr Leu His Ile Pro Arg Ala Gln Val Ser Asp Ser Ala Thr Tyr
                1605                1610                1615
```

```
Thr Cys His Val Ala Asn Val Ala Gly Thr Ala Glu Lys Ser Phe His
            1620                1625                1630

Val Asp Val Tyr Val Pro Pro Met Ile Glu Gly Asn Leu Ala Thr Pro
        1635                1640                1645

Leu Asn Lys Gln Val Val Ile Ala His Ser Leu Thr Leu Glu Cys Lys
    1650                1655                1660

Ala Ala Gly Asn Pro Ser Pro Ile Leu Thr Trp Leu Lys Asp Gly Val
1665                1670                1675                1680

Pro Val Lys Ala Asn Asp Asn Ile Arg Ile Glu Ala Gly Gly Lys Lys
            1685                1690                1695

Leu Glu Ile Met Ser Ala Gln Glu Ile Asp Arg Gly Gln Tyr Ile Cys
        1700                1705                1710

Val Ala Thr Ser Val Ala Gly Glu Lys Glu Ile Lys Tyr Glu Val Asp
    1715                1720                1725

Val Leu Val Pro Pro Ala Ile Glu Gly Gly Asp Glu Thr Ser Tyr Phe
1730                1735                1740

Ile Val Met Val Asn Asn Leu Leu Glu Leu Asp Cys His Val Thr Gly
1745                1750                1755                1760

Ser Pro Pro Pro Thr Ile Met Trp Leu Lys Asp Gly Gln Leu Ile Asp
            1765                1770                1775

Glu Arg Asp Gly Phe Lys Ile Leu Leu Asn Gly Arg Lys Leu Val Ile
        1780                1785                1790

Ala Gln Ala Gln Val Ser Asn Thr Gly Leu Tyr Arg Cys Met Ala Ala
    1795                1800                1805

Asn Thr Ala Gly Asp His Lys Lys Glu Phe Glu Val Thr Val His Val
1810                1815                1820

Pro Pro Thr Ile Lys Ser Ser Gly Leu Ser Glu Arg Val Val Val Lys
1825                1830                1835                1840

Tyr Lys Pro Val Ala Leu Gln Cys Ile Ala Asn Gly Ile Pro Asn Pro
            1845                1850                1855

Ser Ile Thr Trp Leu Lys Asp Asp Gln Pro Val Asn Thr Ala Gln Gly
        1860                1865                1870

Asn Leu Lys Ile Gln Ser Ser Gly Arg Val Leu Gln Ile Ala Lys Thr
    1875                1880                1885

Leu Leu Glu Asp Ala Gly Arg Tyr Thr Cys Val Ala Thr Asn Ala Ala
    1890                1895                1900

Gly Glu Thr Gln Gln His Ile Gln Leu His Val His Glu Pro Pro Ser
1905                1910                1915                1920

Leu Glu Asp Ala Gly Lys Met Leu Asn Glu Thr Val Leu Val Ser Asn
            1925                1930                1935

Pro Val Gln Leu Glu Cys Lys Ala Ala Gly Asn Pro Val Pro Val Ile
        1940                1945                1950

Thr Trp Tyr Lys Asp Asn Arg Leu Leu Ser Gly Ser Thr Ser Met Thr
    1955                1960                1965

Phe Leu Asn Arg Gly Gln Ile Ile Asp Ile Glu Ser Ala Gln Ile Ser
    1970                1975                1980

Asp Ala Gly Ile Tyr Lys Cys Val Ala Ile Asn Ser Ala Gly Ala Thr
1985                1990                1995                2000

Glu Leu Phe Tyr Ser Leu Gln Val His Val Ala Pro Ser Ile Ser Gly
            2005                2010                2015

Ser Asn Asn Met Val Ala Val Val Val Asn Asn Pro Val Arg Leu Glu
        2020                2025                2030
```

-continued

Cys Glu Ala Arg Gly Ile Pro Ala Pro Ser Leu Thr Trp Leu Lys Asp
                2035                2040                2045
Gly Ser Pro Val Ser Ser Phe Ser Asn Gly Leu Gln Val Leu Ser Gly
                2050                2055                2060
Gly Arg Ile Leu Ala Leu Thr Ser Ala Gln Ile Ser Asp Thr Gly Arg
2065                2070                2075                2080
Tyr Thr Cys Val Ala Val Asn Ala Ala Gly Glu Lys Gln Arg Asp Ile
                2085                2090                2095
Asp Leu Arg Val Tyr Val Pro Pro Asn Ile Met Gly Glu Glu Gln Asn
                2100                2105                2110
Val Ser Val Leu Ile Ser Gln Ala Val Glu Leu Leu Cys Gln Ser Asp
                2115                2120                2125
Ala Ile Pro Pro Pro Thr Leu Thr Trp Leu Lys Asp Gly His Pro Leu
                2130                2135                2140
Leu Lys Lys Pro Gly Leu Ser Ile Ser Glu Asn Arg Ser Val Leu Lys
2145                2150                2155                2160
Ile Glu Asp Ala Gln Val Gln Asp Thr Gly Arg Tyr Thr Cys Glu Ala
                2165                2170                2175
Thr Asn Val Ala Gly Lys Thr Glu Lys Asn Tyr Asn Val Asn Ile Trp
                2180                2185                2190
Val Pro Pro Asn Ile Gly Gly Ser Asp Glu Leu Thr Gln Leu Thr Val
                2195                2200                2205
Ile Glu Gly Asn Leu Ile Ser Leu Leu Cys Glu Ser Ser Gly Ile Pro
                2210                2215                2220
Pro Pro Asn Leu Ile Trp Lys Lys Gly Ser Pro Val Leu Thr Asp
2225                2230                2235                2240
Ser Met Gly Arg Xaa Arg Ile Leu Ser Gly Gly Arg Gln Leu Gln Ile
                2245                2250                2255
Ser Ile Ala Glu Lys Ser Asp Ala Ala Leu Tyr Ser Cys Val Ala Ser
                2260                2265                2270
Asn Val Ala Gly Thr Ala Lys Lys Glu Tyr Asn Leu Gln Val Tyr Ile
                2275                2280                2285
Arg Pro Thr Ile Thr Asn Ser Gly Ser His Pro Thr Glu Ile Ile Val
                2290                2295                2300
Thr Arg Gly Lys Ser Ile Ser Leu Glu Cys Glu Val Gln Gly Ile Pro
2305                2310                2315                2320
Pro Pro Thr Val Thr Trp Met Lys Asp Gly His Pro Leu Ile Lys Ala
                2325                2330                2335
Lys Gly Val Glu Ile Leu Asp Glu Gly His Ile Leu Gln Leu Lys Asn
                2340                2345                2350
Ile His Val Ser Asp Thr Gly Arg Tyr Val Cys Val Ala Val Asn Val
                2355                2360                2365
Ala Gly Met Thr Asp Lys Lys Tyr Asp Leu Ser Val His Ala Pro Pro
                2370                2375                2380
Ser Ile Ile Gly Asn His Arg Ser Pro Glu Asn Ile Ser Val Val Glu
2385                2390                2395                2400
Lys Asn Ser Val Ser Leu Thr Cys Glu Ala Ser Gly Ile Pro Leu Pro
                2405                2410                2415
Ser Xaa Thr Trp Phe Lys Asp Gly Trp Pro Val Ser Leu Ser Asn Ser
                2420                2425                2430
Val Arg Ile Leu Ser Gly Gly Arg Met Leu Arg Leu Met Gln Thr Thr
                2435                2440                2445
Met Glu Asp Ala Gly Gln Tyr Thr Cys Val Val Arg Asn Ala Ala Gly

-continued

```
              2450                2455                2460
Glu Glu Arg Lys Ile Phe Gly Leu Ser Val Leu Val Pro Pro His Ile
2465                2470                2475                2480

Val Gly Glu Asn Thr Leu Glu Asp Val Lys Val Lys Glu Lys Gln Ser
                2485                2490                2495

Val Thr Leu Thr Cys Glu Val Thr Gly Asn Pro Val Pro Glu Ile Thr
                2500                2505                2510

Trp His Lys Asp Gly Gln Pro Leu Gln Glu Asp Glu Ala His His Ile
                2515                2520                2525

Ile Ser Gly Gly Arg Phe Leu Gln Ile Thr Asn Val Gln Val Pro His
                2530                2535                2540

Thr Gly Arg Tyr Thr Cys Leu Ala Ser Ser Pro Ala Gly His Lys Ser
2545                2550                2555                2560

Arg Ser Phe Ser Leu Asn Val Phe Val Ser Pro Thr Ile Ala Gly Val
                2565                2570                2575

Gly Ser Asp Gly Asn Pro Glu Asp Val Thr Val Ile Leu Asn Ser Pro
                2580                2585                2590

Thr Ser Leu Val Cys Glu Ala Tyr Ser Tyr Pro Ala Thr Ile Thr
                2595                2600                2605

Trp Phe Lys Asp Gly Thr Pro Leu Glu Ser Asn Arg Asn Ile Arg Ile
                2610                2615                2620

Leu Pro Gly Gly Arg Thr Leu Gln Ile Leu Asn Ala Gln Glu Asp Asn
2625                2630                2635                2640

Ala Gly Arg Tyr Ser Cys Val Ala Thr Asn Glu Ala Gly Glu Met Ile
                2645                2650                2655

Lys His Tyr Glu Val Lys Val Tyr Ile Pro Pro Ile Ile Asn Lys Gly
                2660                2665                2670

Asp Leu Trp Gly Pro Gly Leu Ser Pro Lys Glu Val Lys Ile Lys Val
                2675                2680                2685

Asn Asn Thr Leu Thr Leu Glu Cys Glu Ala Tyr Ala Ile Pro Ser Ala
                2690                2695                2700

Ser Leu Ser Trp Tyr Lys Asp Gly Gln Pro Leu Lys Ser Asp His
2705                2710                2715                2720

Val Asn Ile Ala Ala Asn Gly His Thr Leu Gln Ile Lys Glu Ala Gln
                2725                2730                2735

Ile Ser Asp Thr Gly Arg Tyr Thr Cys Val Ala Ser Asn Ile Ala Gly
                2740                2745                2750

Glu Asp Glu Leu Asp Phe Asp Val Asn Ile Gln Val Pro Pro Ser Phe
                2755                2760                2765

Gln Lys Leu Trp Glu Ile Gly Asn Met Leu Asp Thr Gly Arg Asn Gly
                2770                2775                2780

Glu Ala Lys Asp Val Ile Ile Asn Asn Pro Ile Ser Leu Tyr Cys Glu
2785                2790                2795                2800

Thr Asn Ala Ala Pro Pro Thr Leu Thr Trp Tyr Lys Asp Gly His
                2805                2810                2815

Pro Leu Thr Ser Ser Asp Lys Val Leu Ile Leu Pro Gly Gly Arg Val
                2820                2825                2830

Leu Gln Ile Pro Arg Ala Lys Val Glu Asp Ala Gly Arg Tyr Thr Cys
                2835                2840                2845

Val Ala Val Asn Glu Ala Gly Glu Asp Ser Leu Gln Tyr Asp Val Arg
                2850                2855                2860

Val Leu Val Pro Pro Ile Ile Lys Gly Ala Asn Ser Asp Leu Pro Glu
2865                2870                2875                2880
```

-continued

```
Glu Val Thr Val Leu Val Asn Lys Ser Ala Leu Ile Glu Cys Leu Ser
            2885                2890                2895

Ser Gly Ser Pro Ala Pro Arg Asn Ser Trp Gln Lys Asp Gly Gln Pro
        2900                2905                2910

Leu Leu Glu Asp Asp His His Lys Phe Leu Ser Asn Gly Arg Ile Leu
        2915                2920                2925

Gln Ile Leu Asn Thr Gln Ile Thr Asp Ile Gly Arg Tyr Val Cys Val
        2930                2935                2940

Ala Glu Asn Thr Ala Gly Ser Ala Lys Lys Tyr Phe Asn Leu Asn Val
2945                2950                2955                2960

His Val Pro Pro Ser Val Ile Gly Pro Lys Ser Glu Asn Leu Thr Val
            2965                2970                2975

Val Val Asn Asn Phe Ile Ser Leu Thr Cys Glu Val Ser Gly Phe Pro
            2980                2985                2990

Pro Pro Asp Leu Ser Trp Leu Lys Asn Glu Gln Pro Ile Lys Leu Asn
        2995                3000                3005

Thr Asn Thr Leu Ile Val Pro Gly Gly Arg Thr Leu Gln Ile Ile Arg
    3010                3015                3020

Ala Lys Val Ser Asp Gly Gly Glu Tyr Thr Cys Ile Ala Ile Asn Gln
3025                3030                3035                3040

Ala Gly Glu Ser Lys Lys Lys Phe Ser Leu Thr Val Tyr Val Pro Pro
            3045                3050                3055

Ser Ile Lys Asp His Asp Ser Glu Ser Leu Ser Val Val Asn Val Arg
        3060                3065                3070

Glu Gly Thr Ser Val Ser Leu Glu Cys Glu Ser Asn Ala Val Pro Pro
    3075                3080                3085

Pro Val Ile Thr Trp Tyr Lys Asn Gly Arg Met Ile Thr Glu Ser Thr
    3090                3095                3100

His Val Glu Ile Leu Ala Asp Gly Gln Met Leu His Ile Lys Lys Ala
3105                3110                3115                3120

Glu Val Ser Asp Thr Gly Gln Tyr Val Cys Arg Ala Ile Asn Val Ala
            3125                3130                3135

Gly Arg Asp Asp Lys Asn Phe His Leu Asn Val Tyr Val Pro Pro Ser
        3140                3145                3150

Ile Glu Gly Pro Glu Arg Glu Val Ile Val Glu Thr Ile Ser Asn Pro
        3155                3160                3165

Val Thr Leu Thr Cys Asp Ala Thr Gly Ile Pro Pro Pro Thr Ile Ala
    3170                3175                3180

Trp Leu Lys Asn His Lys Arg Ile Glu Asn Ser Asp Ser Leu Glu Val
3185                3190                3195                3200

Arg Ile Leu Ser Gly Gly Ser Lys Leu Gln Ile Ala Arg Ser Gln His
            3205                3210                3215

Ser Asp Ser Gly Asn Tyr Thr Cys Ile Ala Ser Asn Met Glu Gly Lys
        3220                3225                3230

Ala Gln Lys Tyr Tyr Phe Leu Ser Ile Gln Val Pro Pro Ser Val Ala
        3235                3240                3245

Gly Ala Glu Ile Pro Ser Asp Val Ser Val Leu Leu Gly Glu Asn Val
    3250                3255                3260

Glu Leu Val Cys Asn Ala Asn Gly Ile Pro Thr Pro Leu Ile Gln Trp
3265                3270                3275                3280

Leu Lys Asp Gly Lys Pro Ile Ala Ser Gly Glu Thr Glu Arg Ile Arg
            3285                3290                3295
```

-continued

```
Val Ser Ala Asn Gly Ser Thr Leu Asn Ile Tyr Gly Ala Leu Thr Ser
            3300                3305                3310

Asp Thr Gly Lys Tyr Thr Cys Val Ala Thr Asn Pro Ala Gly Glu Glu
        3315                3320                3325

Asp Arg Ile Phe Asn Leu Asn Val Tyr Val Thr Pro Thr Ile Arg Gly
        3330                3335                3340

Asn Lys Asp Glu Ala Glu Lys Leu Met Thr Leu Val Asp Thr Ser Ile
3345                3350                3355                3360

Asn Ile Glu Cys Arg Ala Thr Gly Thr Pro Pro Gln Ile Asn Trp
            3365                3370                3375

Leu Lys Asn Gly Leu Pro Leu Pro Leu Ser Ser His Ile Arg Leu Leu
            3380                3385                3390

Ala Ala Gly Gln Val Ile Arg Ile Val Arg Ala Gln Val Ser Asp Val
        3395                3400                3405

Ala Val Tyr Thr Cys Val Ala Ser Asn Arg Ala Gly Val Asp Asn Lys
        3410                3415                3420

His Tyr Asn Leu Gln Val Phe Ala Pro Pro Asn Met Asp Asn Ser Met
3425                3430                3435                3440

Gly Thr Glu Glu Ile Thr Val Leu Lys Gly Ser Ser Thr Ser Met Ala
            3445                3450                3455

Cys Ile Thr Asp Gly Thr Pro Ala Pro Ser Met Ala Trp Leu Arg Asp
            3460                3465                3470

Gly Gln Pro Leu Gly Leu Asp Ala His Leu Thr Val Ser Thr His Gly
            3475                3480                3485

Met Val Leu Gln Leu Leu Lys Ala Glu Thr Glu Asp Ser Gly Lys Tyr
            3490                3495                3500

Thr Cys Ile Ala Ser Asn Glu Ala Gly Glu Val Ser Lys His Phe Ile
3505                3510                3515                3520

Leu Lys Val Leu Glu Pro Pro His Ile Asn Gly Ser Glu Glu His Glu
            3525                3530                3535

Glu Ile Ser Val Ile Val Asn Asn Pro Leu Glu Leu Thr Cys Ile Ala
            3540                3545                3550

Ser Gly Ile Pro Ala Pro Lys Met Thr Trp Met Lys Asp Gly Arg Pro
            3555                3560                3565

Leu Pro Gln Thr Asp Gln Val Gln Thr Leu Gly Gly Gly Glu Val Leu
            3570                3575                3580

Arg Ile Ser Thr Ala Gln Val Glu Asp Thr Gly Arg Tyr Thr Cys Leu
3585                3590                3595                3600

Ala Ser Ser Pro Ala Gly Asp Asp Asp Lys Glu Tyr Leu Val Arg Val
            3605                3610                3615

His Val Pro Pro Asn Ile Ala Gly Thr Asp Glu Pro Arg Asp Ile Thr
            3620                3625                3630

Val Leu Arg Asn Arg Gln Val Thr Leu Glu Cys Lys Ser Asp Ala Val
            3635                3640                3645

Pro Pro Pro Val Ile Thr Trp Leu Arg Asn Gly Glu Arg Leu Gln Ala
            3650                3655                3660

Thr Pro Arg Val Arg Ile Leu Ser Gly Gly Arg Tyr Leu Gln Ile Asn
3665                3670                3675                3680

Asn Ala Asp Leu Gly Asp Thr Ala Asn Tyr Thr Cys Val Ala Ser Asn
            3685                3690                3695

Ile Ala Gly Lys Thr Thr Arg Glu Phe Ile Leu Thr Val Asn Val Pro
            3700                3705                3710

Pro Asn Ile Lys Gly Gly Pro Gln Ser Leu Val Ile Leu Leu Asn Lys
```

```
                    3715              3720              3725
Ser Thr Val Leu Glu Cys Ile Ala Glu Gly Val Pro Thr Pro Arg Ile
    3730              3735              3740

Thr Trp Arg Lys Asp Gly Ala Val Leu Ala Gly Asn His Ala Arg Tyr
3745              3750              3755              3760

Ser Ile Leu Glu Asn Gly Phe Leu His Ile Gln Ser Ala His Val Thr
                  3765              3770              3775

Asp Thr Gly Arg Tyr Leu Cys Met Ala Thr Asn Ala Ala Gly Thr Asp
            3780              3785              3790

Arg Arg Arg Ile Asp Leu Gln Val His Val Pro Pro Ser Ile Ala Pro
        3795              3800              3805

Gly Pro Thr Asn Met Thr Val Ile Val Asn Val Gln Thr Thr Leu Ala
    3810              3815              3820

Cys Glu Ala Thr Gly Ile Pro Lys Pro Ser Ile Asn Trp Arg Lys Asn
3825              3830              3835              3840

Gly His Leu Leu Asn Val Asp Gln Asn Gln Asn Ser Tyr Arg Leu Leu
                  3845              3850              3855

Ser Ser Gly Ser Leu Val Ile Ile Ser Pro Ser Val Asp Asp Thr Ala
            3860              3865              3870

Thr Tyr Glu Cys Thr Val Thr Asn Gly Ala Gly Asp Asp Lys Arg Thr
        3875              3880              3885

Val Asp Leu Thr Val Gln Val Pro Pro Ser Ile Ala Asp Glu Pro Thr
    3890              3895              3900

Asp Phe Leu Val Thr Lys His Ala Pro Ala Val Ile Thr Cys Thr Ala
3905              3910              3915              3920

Ser Gly Val Pro Phe Pro Ser Ile His Trp Thr Lys Asn Gly Ile Arg
                  3925              3930              3935

Leu Leu Pro Arg Gly Asp Gly Tyr Arg Ile Leu Ser Ser Gly Ala Ile
            3940              3945              3950

Glu Ile Leu Ala Thr Gln Leu Asn His Ala Gly Arg Tyr Thr Cys Val
        3955              3960              3965

Ala Arg Asn Ala Ala Gly Ser Ala His Arg His Val Thr Leu His Val
    3970              3975              3980

His Glu Pro Pro Val Ile Gln Pro Gln Pro Ser Glu Leu His Val Ile
3985              3990              3995              4000

Leu Asn Asn Pro Ile Leu Leu Pro Cys Glu Ala Thr Gly Thr Pro Ser
                  4005              4010              4015

Pro Phe Ile Thr Trp Gln Lys Glu Gly Ile Asn Val Asn Thr Ser Gly
            4020              4025              4030

Arg Asn His Ala Val Leu Pro Ser Gly Leu Gln Ile Xaa Arg Ala
        4035              4040              4045

Val Arg Glu Asp Ala Gly Thr Tyr Met Cys Val Ala Gln Asn Pro Ala
    4050              4055              4060

Gly Thr Ala Leu Gly Lys Ile Lys Leu Asn Val Gln Val Pro Pro Val
4065              4070              4075              4080

Ile Ser Pro His Leu Lys Glu Tyr Val Ile Ala Val Asp Lys Pro Ile
                  4085              4090              4095

Thr Leu Ser Cys Glu Ala Asp Gly Leu Pro Pro Pro Asp Ile Thr Trp
            4100              4105              4110

His Lys Asp Gly Arg Ala Ile Val Glu Ser Ile Arg Gln Arg Val Leu
        4115              4120              4125

Ser Ser Gly Ser Leu Gln Ile Ala Phe Val Gln Pro Gly Asp Ala Gly
    4130              4135              4140
```

-continued

```
His Tyr Thr Cys Met Ala Ala Asn Val Ala Gly Ser Ser Thr Ser
4145                4150                4155                4160

Thr Lys Leu Thr Val His Val Pro Pro Arg Ile Arg Ser Thr Glu Gly
            4165                4170                4175

His Tyr Thr Val Asn Glu Asn Ser Gln Ala Ile Leu Pro Cys Val Ala
            4180                4185                4190

Asp Gly Ile Pro Thr Pro Ala Ile Asn Trp Lys Lys Asp Asn Val Leu
            4195                4200                4205

Leu Ala Asn Leu Leu Gly Lys Tyr Thr Ala Glu Pro Tyr Gly Glu Leu
4210                4215                4220

Ile Leu Glu Asn Val Val Leu Glu Asp Ser Gly Phe Tyr Thr Cys Val
4225                4230                4235                4240

Ala Asn Asn Ala Ala Gly Glu Asp Thr His Thr Val Ser Leu Thr Val
                4245                4250                4255

His Val Leu Pro Thr Phe Thr Glu Leu Pro Gly Asp Val Ser Leu Asn
                4260                4265                4270

Lys Gly Glu Gln Leu Arg Leu Ser Cys Lys Ala Thr Gly Ile Pro Leu
                4275                4280                4285

Pro Lys Leu Thr Trp Thr Phe Asn Asn Asn Ile Ile Pro Ala His Phe
4290                4295                4300

Asp Ser Val Asn Gly His Ser Glu Leu Val Ile Glu Arg Val Ser Lys
4305                4310                4315                4320

Glu Asp Ser Gly Thr Tyr Val Cys Thr Ala Glu Asn Ser Val Gly Phe
                4325                4330                4335

Val Lys Ala Ile Gly Phe Val Tyr Val Lys Glu Pro Pro Val Phe Lys
                4340                4345                4350

Gly Asp Tyr Pro Ser Asn Trp Ile Glu Pro Leu Gly Gly Asn Ala Ile
                4355                4360                4365

Leu Asn Cys Glu Val Lys Gly Asp Pro Thr Pro Thr Ile Gln Trp Asn
4370                4375                4380

Arg Lys Gly Val Asp Ile Glu Ile Ser His Arg Ile Arg Gln Leu Gly
4385                4390                4395                4400

Asn Gly Ser Leu Ala Ile Tyr Gly Thr Val Asn Glu Asp Ala Gly Asp
                4405                4410                4415

Tyr Thr Cys Val Ala Thr Asn Glu Ala Gly Val Val Glu Arg Ser Met
                4420                4425                4430

Ser Leu Thr Leu Gln Ser Pro Pro Ile Ile Thr Leu Glu Pro Val Glu
                4435                4440                4445

Thr Val Ile Asn Ala Gly Gly Lys Ile Ile Leu Asn Cys Gln Ala Thr
4450                4455                4460

Gly Glu Pro Gln Pro Thr Ile Thr Trp Ser Arg Gln Gly His Ser Ile
4465                4470                4475                4480

Ser Trp Asp Asp Arg Val Asn Val Leu Ser Asn Asn Ser Leu Tyr Ile
                4485                4490                4495

Ala Asp Ala Gln Lys Glu Asp Thr Ser Glu Phe Glu Cys Val Ala Arg
                4500                4505                4510

Asn Leu Met Gly Ser Val Leu Val Arg Val Pro Val Ile Val Gln Val
                4515                4520                4525

His Gly Gly Phe Ser Gln Trp Ser Ala Trp Arg Ala Cys Ser Val Thr
                4530                4535                4540

Cys Gly Lys Gly Ile Gln Lys Arg Ser Arg Leu Cys Asn Gln Pro Leu
4545                4550                4555                4560
```

```
Pro Ala Asn Gly Gly Lys Pro Cys Gln Gly Ser Asp Leu Glu Met Arg
                4565                4570                4575

Asn Cys Gln Asn Lys Pro Cys Pro Val Asp Gly Ser Trp Ser Glu Trp
            4580                4585                4590

Ser Leu Trp Glu Glu Cys Thr Arg Ser Cys Gly Arg Gly Asn Gln Thr
        4595                4600                4605

Arg Thr Arg Thr Cys Asn Asn Pro Ser Val Gln His Gly Gly Arg Pro
    4610                4615                4620

Cys Glu Gly Asn Ala Val Glu Ile Ile Met Cys Asn Ile Arg Pro Cys
4625                4630                4635                4640

Pro Val His Gly Ala Trp Ser Ala Trp Gln Pro Trp Gly Thr Cys Ser
                4645                4650                4655

Glu Ser Cys Gly Lys Gly Thr Gln Thr Arg Ala Arg Leu Cys Asn Asn
            4660                4665                4670

Pro Pro Pro Ala Phe Gly Gly Ser Tyr Cys Asp Gly Ala Glu Thr Gln
        4675                4680                4685

Met Gln Val Cys Asn Glu Arg Asn Cys Pro Ile His Gly Lys Trp Ala
    4690                4695                4700

Thr Trp Ala Ser Trp Ser Ala Cys Ser Val Ser Cys Gly Gly Gly Ala
4705                4710                4715                4720

Arg Gln Arg Thr Arg Gly Cys Ser Asp Pro Val Pro Gln Tyr Gly Gly
                4725                4730                4735

Arg Lys Cys Glu Gly Ser Asp Val Gln Ser Asp Phe Cys Asn Ser Asp
            4740                4745                4750

Pro Cys Pro Thr His Gly Asn Trp Ser Pro Trp Ser Gly Trp Gly Thr
        4755                4760                4765

Cys Ser Arg Thr Cys Asn Gly Gly Gln Met Arg Arg Tyr Arg Thr Cys
    4770                4775                4780

Asp Asn Pro Pro Pro Ser Asn Gly Gly Arg Ala Cys Gly Gly Pro Asp
4785                4790                4795                4800

Ser Gln Ile Gln Arg Cys Asn Thr Asp Met Cys Pro Val Asp Gly Ser
                4805                4810                4815

Trp Gly Ser Trp His Ser Trp Ser Gln Cys Ser Ala Ser Cys Gly Gly
            4820                4825                4830

Gly Glu Lys Thr Arg Lys Arg Leu Cys Asp His Pro Val Pro Val Lys
        4835                4840                4845

Gly Gly Arg Pro Cys Pro Gly Asp Thr Thr Gln Val Thr Arg Cys Asn
    4850                4855                4860

Val Gln Ala Cys Pro Gly Gly Pro Gln Arg Ala Arg Gly Ser Val Ile
4865                4870                4875                4880

Gly Asn Ile Asn Asp Val Glu Phe Gly Ile Ala Phe Leu Asn Ala Thr
                4885                4890                4895

Ile Thr Asp Ser Pro Asn Ser Asp Thr Arg Ile Ile Arg Ala Lys Ile
            4900                4905                4910

Thr Asn Val Pro Arg Ser Leu Gly Ser Ala Met Arg Lys Ile Val Ser
        4915                4920                4925

Ile Leu Asn Pro Ile Tyr Trp Thr Thr Ala Lys Glu Ile Gly Glu Ala
    4930                4935                4940

Val Asn Gly Phe Thr Leu Thr Asn Ala Val Phe Lys Arg Glu Thr Gln
4945                4950                4955                4960

Val Glu Phe Ala Thr Gly Glu Ile Leu Gln Met Ser His Ile Ala Arg
                4965                4970                4975

Gly Leu Asp Ser Asp Gly Ser Leu Leu Leu Asp Ile Val Val Ser Gly
```

-continued

```
                4980              4985              4990
Tyr Val Leu Gln Leu Gln Ser Pro Ala Glu Val Thr Val Lys Asp Tyr
        4995              5000              5005

Thr Glu Asp Tyr Ile Gln Thr Gly Pro Gly Gln Leu Tyr Ala Tyr Ser
    5010              5015              5020

Thr Arg Leu Phe Thr Ile Asp Gly Ile Ser Ile Pro Tyr Thr Trp Asn
5025              5030              5035              5040

His Thr Val Phe Tyr Asp Gln Ala Gln Gly Arg Met Pro Phe Leu Val
            5045              5050              5055

Glu Thr Leu His Ala Ser Ser Val Glu Ser Asp Tyr Asn Gln Ile Glu
        5060              5065              5070

Glu Thr Leu Gly Phe Lys Ile His Ala Ser Ile Ser Lys Gly Asp Arg
        5075              5080              5085

Ser Asn Gln Cys Pro Ser Gly Phe Thr Leu Asp Ser Val Gly Pro Phe
    5090              5095              5100

Cys Ala Asp Glu Asp Glu Cys Ala Ala Gly Asn Pro Cys Ser His Ser
5105              5110              5115              5120

Cys His Asn Ala Met Gly Thr Tyr Tyr Cys Ser Cys Pro Lys Gly Leu
            5125              5130              5135

Thr Ile Ala Ala Asp Gly Arg Thr Cys Gln Asp Ile Asp Glu Cys Ala
            5140              5145              5150

Leu Gly Arg His Thr Cys His Ala Gly Gln Asp Cys Asp Asn Thr Ile
        5155              5160              5165

Gly Ser Tyr Arg Cys Val Val Arg Cys Gly Ser Gly Phe Arg Arg Thr
    5170              5175              5180

Ser Asp Gly Leu Ser Cys Gln Asp Ile Asn Glu Cys Gln Glu Ser Ser
5185              5190              5195              5200

Pro Cys His Gln Arg Cys Phe Asn Ala Ile Gly Ser Phe His Cys Gly
            5205              5210              5215

Cys Glu Pro Gly Tyr Gln Leu Lys Gly Arg Lys Cys Met Asp Val Asn
        5220              5225              5230

Glu Cys Arg Gln Asn Val Cys Arg Pro Asp Gln His Cys Lys Asn Thr
        5235              5240              5245

Arg Gly Gly Tyr Lys Cys Ile Asp Leu Cys Pro Asn Gly Met Thr Lys
    5250              5255              5260

Ala Glu Asn Gly Thr Cys Ile Asp Ile Asp Glu Cys Lys Asp Gly Thr
5265              5270              5275              5280

His Gln Cys Arg Tyr Asn Gln Ile Cys Glu Asn Thr Arg Gly Ser Tyr
            5285              5290              5295

Arg Cys Val Cys Pro Arg Gly Tyr Arg Ser Gln Gly Val Gly Arg Pro
        5300              5305              5310

Cys Met Asp Ile Asp Glu Cys Glu Asn Thr Asp Ala Cys Gln His Glu
    5315              5320              5325

Cys Lys Asn Thr Phe Gly Ser Tyr Gln Cys Ile Cys Pro Pro Gly Tyr
    5330              5335              5340

Gln Leu Thr His Asn Gly Lys Thr Cys Gln Asp Ile Asp Glu Cys Leu
5345              5350              5355              5360

Glu Gln Asn Val His Cys Gly Pro Asn Arg Met Cys Phe Asn Met Arg
            5365              5370              5375

Gly Ser Tyr Gln Cys Ile Asp Thr Pro Cys Pro Asn Tyr Gln Arg
        5380              5385              5390

Asp Pro Val Ser Gly Phe Cys Leu Lys Asn Cys Pro Pro Asn Asp Leu
    5395              5400              5405
```

```
Glu Cys Ala Leu Ser Pro Tyr Ala Leu Glu Tyr Lys Leu Val Ser Leu
    5410                5415                5420

Pro Phe Gly Ile Ala Thr Asn Gln Asp Leu Ile Arg Leu Val Ala Tyr
5425                5430                5435                5440

Thr Gln Asp Gly Val Met His Pro Arg Thr Thr Phe Leu Met Val Asp
                5445                5450                5455

Glu Glu Gln Thr Val Pro Phe Ala Leu Arg Asp Glu Asn Leu Lys Gly
            5460                5465                5470

Val Val Tyr Thr Thr Arg Pro Leu Arg Glu Ala Glu Thr Tyr Arg Met
        5475                5480                5485

Arg Val Arg Ala Ser Ser Tyr Ser Ala Asn Gly Thr Ile Glu Tyr Gln
    5490                5495                5500

Thr Thr Phe Ile Val Tyr Ile Ala Val Ser Ala Tyr Pro Tyr
5505                5510                5515

<210> SEQ ID NO 3
<211> LENGTH: 12381
<212> TYPE: DNA
<213> ORGANISM: homo sapiens

<400> SEQUENCE: 3
```

| | | | | | |
|---|---|---|---|---|---|
| atgtggtata | aagataatgt | ccaggtgact | gaaagcagca | ctattcagac | tgtgaacaat | 60 |
| gggaagatac | tgaagctctt | cagagccact | ccagaggatg | caggaagata | ttcctgcaaa | 120 |
| gcaattaata | ttgcaggcac | ttctcagaag | tactttaaca | ttgatgtgct | agttccaccc | 180 |
| accataatag | gtaccaactt | cccaaatgaa | gtctcagttg | tcctcaaccg | tgacgtcgcc | 240 |
| cttgaatgcc | aggtcaaagg | cactcccttt | cctgatattc | attggttcaa | agatggcaag | 300 |
| ccttttatttt | tgggcgatcc | taatgttgaa | cttctagaca | gaggacaagt | cttacattta | 360 |
| aagaatgcac | ggagaaatga | caaggggcgc | taccaatgta | ctgtgtctaa | tgcagctggc | 420 |
| aaacaagcca | aggatataaa | actgactatc | tatattccac | tagtattaa | aggaggaaat | 480 |
| gtcaccacrg | mcatatcagt | attgatcaac | agccttatta | aactggaatg | tgaaacacgg | 540 |
| ggacttccaa | tgcctgccat | tacttggtat | aaggacgggc | agccaatcat | gtccagctca | 600 |
| caagcacttt | tatattgataa | aggacaatat | cttcatattc | ctcgagcaca | ggtctctgat | 660 |
| tcagcaacat | atacgtgtca | ytagccaat | gttgctggaa | ctgctgaaaa | atcattccat | 720 |
| gtggatgtct | atgttcctcc | aatgattgaa | ggcaacttgg | ccacgccttt | gaataagcaa | 780 |
| gtagttattg | ctcattctct | gacactggag | tgcaaagctg | ctggaaaccc | ttctcccatt | 840 |
| ctcacctggt | tgaaagatgg | tgtacctgtg | aaagctaatg | acaatatccg | catagaagct | 900 |
| ggtgggaaga | aactcgaaat | catgagtgcc | caagaaattg | atcgaggaca | gtacatatgc | 960 |
| gtggctacca | gtgtggcagg | agaaaaggaa | atcaaatatg | aagttgatgt | cttggtgcca | 1020 |
| ccagctatag | aaggaggaga | tgaaacatct | tacttcattg | tgatggttaa | taacttactg | 1080 |
| gagctagatt | gtcatgtgac | aggctctccc | ccaccaacta | tcatgtggct | gaaggatggc | 1140 |
| cagtaattg | atgaaaggga | tggattcaag | attttattaa | atggacgcaa | actggttatt | 1200 |
| gctcaggctc | aagtgtcaaa | cacaggcctt | tatcggtgca | tggcagcaaa | tactgctgga | 1260 |
| gaccacaaga | aggaatttga | agtgactgtt | catgttcctc | caacaatcaa | gtcctcaggc | 1320 |
| ctttctgaga | gagttgtggt | aaaatacaag | cctgtcgcct | tgcagtgcat | agccaatggg | 1380 |
| attccaaatc | cttccattac | atggttaaaa | gatgaccagc | tgtgtaacac | tgcccaagga | 1440 |
| aaccttaaaa | tacagtcttc | tggtcgagtt | ctacaaattg | ccaaaaccct | gttggaagat | 1500 |

```
gctggcagat acacatgtgt ggctaccaac gcagctggag aaacacaaca gcacattcaa   1560
ctgcatgttc atgaaccacc tagtctggaa gatgctggaa aaatgctgaa tgagactgtg   1620
ttggtgagca accctgtaca gctggagtgt aaggcagctg aaatcctgt gcctgttatt    1680 acatggtaca agataatcg tctactctca ggttccacca gcatgacttt cttgaacaga    1740
ggacagatca ttgatattga agtgcccag atctcagatg ctggcatata aaatgcgtg     1800 gccatcaact cagctggagc tacagagtta ttttacagtc tgcaagttca tgtggcccca   1860
tcaatttctg gcagcaataa catggtggca gtggtggtta ataacccggt gaggttagaa   1920
tgtgaagcca gaggtattcc tgccccaagt ctgacctggt tgaaagatgg gagtcctgtt   1980
tctagttttt ctaatggatt acaggttctc tctggtggtc gaatcctagc attgaccagt   2040
gcacaaatca gcgacacagg aaggtacacc tgcgtggcag tgaatgctgc tggagaaaag   2100
caaagggaca ttgacctccg agtatatgtt ccgccaaata ttatgggaga gaacagaat    2160 gtctctgtcc tcattagcca agctgtggaa ttactatgtc aaagtgatgc tattccccca   2220
cctactctta cttggttaaa agacggccac cccttgctga gaaaccagg cctcagtata    2280 tctgaaaata gaagtgtgtt aaagattgaa gatgctcagg ttcaagacac tggtcgttac   2340
acttgtgaag caacaaatgt tgctggaaaa actgaaaaaa actacaatgt caacatttgg   2400 gtcccccaa atattggtgg ttctgatgaa cttactcaac ttacagtcat tgaagggaat    2460
ctcattagtc tgttgtgtga atcaagtggt attccacccc caaatctcat ctggaagaag   2520
aaaggctctc cagtgctgac tgattccatg gggcgagyta gaattttatc tggggggcagg  2580 caattacaaa tttcaattgc tgaaaagtct gatgcagcac tctattcatg tgtggcgtcg   2640
aatgttgctg ggactgcaaa gaaagaatac aatctgcaag tttacattag accaaccata   2700
accaacagtg gcagccaccc tactgaaatt attgtgaccc gagggaagag tatctccttg   2760
gagtgtgagg tgcagggtat tccaccacca acagtgacct ggatgaaaga tggccacccc   2820
ttgatcaagg caaagggagt agaaatactg gatgaaggtc acatccttca gctgaagaac   2880
attcatgtat ctgacacagg ccgttatgtg tgtgttgctg tgaatgtagc aggaatgact   2940
gacaaaaaat atgacttaag tgtccatgct cctccaagca tcataggaaa ccacaggtca   3000
cctgaaaata ttagtgtggt agaaaagaac tcagtatctt tgacttgtga agcttctgga   3060
attcccctgc cttccayaac ctggttcaaa gatgggtggc ctgtcagcct tagcaattct   3120
gtgaggattc tttcaggagg caggatgcta cggctgatgc agaccacaat ggaagatgct   3180
ggccaatata cttgcgttgt aaggaatgca gctggtgaag aaagaaaaat ctttgggctt   3240
tcagtattag taccacctca tattgtgggt gaaaatacat ggaagatgt gaaggtaaaa   3300 gagaaacaga gtgttacgct gacttgtgaa gtgacaggga atccagtgcc agaaattaca   3360
tggcacaaag atgggcagcc cctccaagaa gatgaagccc atcacattat atctggtggc   3420
cgttttcttc aaattaccaa tgtccaggtg ccacacactg gaagatatac atgtttggct   3480
tccagtccag ctggccacaa gagcaggagc ttcagtctta atgtatttgt atctcctaca   3540
attgctggtg taggtagtga tggcaaccct gaagatgtca ctgtcatcct taacagccct   3600
acatctttgg tctgtgaagc ttattcatat cctccagcta ccatcacctg gtttaaggat   3660
ggcactcctt tagaatctaa ccgaaatatt cgtattcttc aggaggcag aactctgcag    3720 atcctcaatg cacaggagga caatgctgga agatactctt gtgtagccac gaatgaggct   3780
ggagaaatga taaagcacta tgaagtgaag gtgtacattg cacccataat caataaaggg   3840
```

```
gacctttggg ggccaggtct ttcccctaaa gaagtgaaga tcaaagtaaa caacactctg   3900
accttggaat gtgaagcgta tgcaattcct tctgcctccc tcagctggta caaggatgga   3960
cagcccctta aatccgatga tcatgttaat attgctgcga atggacacac acttcaaata   4020
aaggaggctc aaatatcaga caccggacga tatacttgtg tagcatctaa cattgcaggt   4080
gaagatgagt tggattttga tgtgaatatt caagttcctc caagttttca gaaactctgg   4140
gaaataggaa acatgctaga tactggcagg aatggtgaag ccaaagatgt gatcatcaac   4200
aatcccattt ctctttactg tgagacaaat gctgctcccc ctcctacact gacatggtac   4260
aaagatggcc accctctgac ctcaagtgat aaagtattga ttttgccagg agggcgagtg   4320
ttgcagattc ctcgggctaa agtagaagat gctgggagat acacatgtgt ggctgtgaat   4380
gaggctggag aagattccct tcaatatgat gtccgtgtac tcgtgccgcc aattatcaag   4440
ggagcaaata gtgatctccc tgaagaggtc accgtgctgg tgaacaagag tgcactgata   4500
gagtgtttat ccagtggcag cccagcacca aggaattcct ggcagaaaga tggacagccc   4560
ttgctagaag atgaccatca taaatttcta tctaatggac gaattctgca gattctgaat   4620
actcaaataa cagatatcgg caggtatgtg tgtgttgctg agaacacagc tgggagtgcc   4680
aaaaaatatt ttaacctcaa tgttcatgtt cctccaagtg tcattggtcc taaatctgaa   4740
aatcttaccg tcgtggtgaa caatttcatc tctttgacct gtgaggtctc tggttttcca   4800
cctcctgacc tcagctggct caagaatgaa cagcccatca aactgaacac aaatactctc   4860
attgtgcctg tggtcgaaac tctacagatt attcgggcca aggtatcaga tggtggtgaa   4920
tacacttgta tagctatcaa tcaagctggc gaaagcaaga aaaagttttc cctgactgtt   4980
tatgtgcccc caagcattaa agaccatgac agtgaatctc tttctgtagt taatgtaaga   5040 gagggaacttc tgtgtctttt ggagtgtgag tcgaacgctg tgccacctcc agtcatcact   5100
tggtataaga atgggcggat gataacagag tctactcatg tggagatttt agctgatgga   5160
caaatgctac acattaagaa agctgaggta tctgacacag gccagtatgt atgtagagct   5220
ataaatgtag caggacggga tgataaaaat ttccacctca atgtatatgt gccacccagt   5280
attgaaggac ctgaaagaga agtgattgtg gagacgatca gcaatcctgt gacattaaca   5340
tgtgatgcca ctgggatccc acctcccacg atagcatggt taaagaacca caagcgcata   5400
gaaaattctg actcactgga agttcgtatt ttgtctggag gtagcaaact ccagattgcc   5460
cggtctcagc attcagatag tggaaactat acatgtattg cttcaaatat ggagggaaaa   5520
gcccagaaat attactttct ttcaattcaa gttcctccaa gtgttgctgg tgctgaaatt   5580
ccaagtgatg tcagtgtcct tctaggagaa aatgttgagc tggtctgcaa tgcaaatggc   5640
attcctactc cacttattca atggcttaaa gatggaaagc ccatagctag tggtgaaaca   5700
gaaagaatcc gagtgagtgc aaatggcagc acattaaaca tttatggagc tcttacatct   5760
gacacgggga aatacacatg tgttgctact aatcccgctg agaagaaga ccgaattttt   5820 aacttgaatg tctatgttac acctacaatt aggggtaata agatgaagc agagaaacta   5880 atgactttag tggatacttc aataaatatt gaatgcagag ccacagggac gcctccacca   5940
cagataaact ggctgaagaa tggacttcct ctgcctctct cctcccatat ccggttactg   6000
gcagcaggac aagttatcag gattgtgaga gctcaggtgt ctgatgtcgc tgtgtatact   6060
tgtgtggcct ccaacagagc tggggtggat aataagcatt acaatcttca agtgtttgca   6120
ccaccaaata tggacaattc aatggggaca gaggaaatca cagttctcaa aggtagttcc   6180
acctctatgg catgcattac tgatggaacc ccagctccca gtatggcctg cttagagat    6240
```

-continued

```
ggccagcctc tggggcttga tgcccatctg acagtcagca cccatggaat ggtcctgcag    6300
ctcctcaaag cagagactga agattcggga agtacacct gcattgcctc aaatgaagct     6360
ggagaagtca gcaagcactt tatcctcaag gtcctagaac cacctcacat taatggatct    6420
gaagaacatg aagagatatc agtaattgtt ataacccac ttgaacttac ctgcattgct     6480
tctggaatcc cagcccctaa aatgacctgg atgaaagatg gccggcccct tccacagacg    6540
gatcaagtgc aaactctagg aggaggagag gttcttcgaa tttctactgc tcaggtggag    6600
gatacaggaa gatatacatg tctggcatcc agtcctgcag gagatgatga taaggaatat    6660
ctagtgagag tgcatgtacc tcctaatatt gctggaactg atgagccccg ggatatcact    6720
gtgttacgga acagacaagt gacattggaa tgcaagtcag atgcagtgcc cccacctgta    6780
attacttggc tcagaaatgg agaacggtta caggcaacac ctcgagtgcg aatcctatct    6840
ggagggagat acttgcaaat caacaatgct gacctaggtg atacagccaa ttatacctgt    6900
gttgccagca acattgcagg aaagactaca agagaattta ttctcactgt aaatgttcct    6960
ccaaacataa agggggccc ccagagcctt gtaattcttt taaataagtc aactgtattg      7020
gaatgcatcg ctgaaggtgt gccaactcca aggataacat ggagaaagga tggagctgtt    7080
ctagctggga atcatgcaag atattccatc ttggaaaatg gattccttca tattcaatca    7140
gcacatgtca ctgacactgg acggtatttg tgtatggcca ccaatgctgc tggaacagat    7200
cgcaggcgaa tagatttaca ggtccatgtt cctccatcta ttgctccggg tcctaccaac    7260
atgactgtaa tagtaaatgt tcaaactact ctggcttgtg aggctactgg gataccaaaa    7320
ccatcaatca attggagaaa aaatgggcat cttcttaatg tggatcaaaa tcagaactca    7380
tacaggctcc tttcttcagg ttcactagta attatttccc cttctgtgga tgacactgca    7440
acctatgaat gtactgtgac aaacggtgct ggagatgata aagaactgt ggatctcact     7500 gtccaagttc caccttccat agctgatgag cctacagatt tcctagtaac caaacatgcc    7560
ccagcagtaa ttacctgcac tgcttcggga gttccatttc cctcaattca ctggaccaaa    7620
aatggtataa gactgcttcc caggggagat ggctatagaa ttctgtcctc aggagcaatt    7680
gaaatacttg ccacccaatt aaaccatgct ggaagataca cttgtgtcgc taggaatgcg    7740
gctggctctg cacatcgaca cgtsaccctt catgttcatg agcctccagt cattcagccc    7800
caaccaagtg aactacacgt cattctgaac aatcctattt tattaccatg tgaagcaaca    7860
gggacaccca gtcctttcat tacttggcaa aaagaaggca tcaatgttaa cacttcaggc    7920
agaaaccatg cagttcttcc tagtggcggc ttacagatcw ccagagctgt ccgagaggat    7980
gctggcactt acatgtgtgt ggcccagaac ccggctggta cagccttggg caaaatcaag    8040
ttaaatgtcc aagttcctcc agtcattagc cctcatctaa aggaatatgt tattgctgtg    8100
gacaagccca tcacgttatc ctgtgaagca gatggcctcc ctccgcctga cattacatgg    8160
cataaagatg ggcgtgcaat tgtggaatct atccgccagc gcgtcctcag ctctggctct    8220
ctgcaaatag catttgtcca gcctggtgat gctggccatt acacgtgcat ggcagccaat    8280
gtagcaggat caagcagcac aagcaccaag ctcaccgtcc atgtaccacc caggatcaga    8340
agtacagaag gacactacac ggtcaatgag aattcacaag ccattcttcc atgcgtagct    8400
gatggaatcc ccacaccagc aattaactgg aaaaaagaca atgttctttt agctaacttg    8460
ttaggaaaat acactgctga accatatgga gaactcattt tagaaaatgt gtgctggag     8520 gattctggct tctataccctg tgttgctaac aatgctgcag gtgaagatac acacactgtc   8580
```

```
agcctgactg tgcatgttct ccccactttt actgaacttc ctggagacgt gtcattaaat    8640
aaaggagaac agctacgatt aagctgtaaa gctactggta ttccattgcc caaattaaca    8700
tggaccttca ataacaatat tattccagcc cactttgaca gtgtgaatgg acacagtgaa    8760
cttgttattg aaagagtgtc aaaagaggat tcaggtactt atgtgtgcac cgcagagaac    8820
agcgttggct ttgtgaaggc aattggattt gtttatgtga agaacctcc agtcttcaaa    8880 ggtgattatc cttctaactg gattgaacca cttggtggga atgcaatcct gaattgtgag    8940
gtgaaaggag accccacccc aaccatccag tggaacagaa agggagtgga tattgaaatt    9000
agccacagaa tccggcaact gggcaatggc tccctggcca tctatggcac tgttaatgaa    9060
gatgccggtg actatacatg tgtagctacc aatgaagctg gggtggtgga gcgcagcatg    9120
agtctgactc tgcaaagtcc tcctattatc actcttgagc cagtggaaac tgttattaat    9180
gctggtggca aaatcatatt gaattgtcag gcaactggag agcctcaacc aaccattaca    9240
tggtcccgtc aagggcactc tatttcctgg gatgaccggg ttaacgtgtt gtccaacaac    9300
tcattatata ttgctgatgc tcagaaagaa gatacctctg aatttgaatg tgttgctcga    9360
aacttaatgg gttctgtcct tgtcagagtg ccagtcatag tccaggttca tggtggattt    9420
tcccagtggt ctgcatggag agcctgcagt gtcacctgtg gaaaaggcat ccaaaagagg    9480
agtcgtctgt gcaaccagcc ccttccagcc aatggtggga agccctgcca aggttcagat    9540
ttggaaatgc gaaactgtca aaataagcct tgtccagtgg atggtagctg gtcggaatgg    9600
agtctttggg aagaatgcac aaggagctgt ggacgcggca accaaaccag gaccaggact    9660
tgcaataatc catcagttca gcatggtggg cggccatgtg aagggaatgc tgtggaaata    9720
attatgtgca acattaggcc ttgcccagtt catggagcat ggagcgcttg gcagccttgg    9780
ggaacatgca gcgaaagttg tgggaaaggt actcagacaa gagcaagact ttgtaataac    9840
ccaccaccag cgtttggtgg gtcctactgt gatggagcag aaacacagat gcaagtttgc    9900
aatgaaagaa attgtccaat tcatggcaag tgggcgactt gggccagttg gagtgcctgt    9960
tctgtgtcat gtggaggagg tgccagacag agaacaaggg gctgctccga ccctgtgccc   10020 cagtatgag gaaggaaatg cgaagggagt gatgtccaga gtgattttt caacagtgac   10080 ccttgcccaa cccatggtaa ctggagtcct tggagtggct ggggaacatg cagccggacg   10140
tgtaacggag ggcagatgcg gcggtaccgc acatgtgata accctcctcc ctccaatggg   10200
ggaagagctt gtgggggacc agactcccag atccagaggt gcaacactga catgtgtcct   10260
gtggatggaa gttggggaag ctggcatagt tggagccagt gctctgcctc ctgtggagga   10320
ggtgaaaaga ctcggaagcg gctgtgcgac catcctgtgc cagttaaagg tggccgtccc   10380
tgtcccggag acactactca ggtgaccagg tgcaatgtac aagcatgtcc aggtgggccc   10440
cagcgagcca gaggaagtgt tattggaaat attaatgatg ttgaatttgg aattgctttc   10500
cttaatgcca caataactga tagccctaac tctgatacta gaataatacg tgccaaaatt   10560
accaatgtac ctcgtagtct tggttcagca atgagaaaga tagtttctat tctaaatccc   10620
atttattgga caacagcaaa ggaaatagga gaagcagtca atggctttac cctcaccaat   10680
gcagtcttca aaagagaaac tcaagtggaa tttgcaactg gagaaatctt gcagatgagt   10740
catattgccg ggggcttgga ttccgatggt tcttttgctgc tagatatcgt tgtgagtggc   10800
tatgtcctac agcttcagtc acctgctgaa gtcactgtaa aggattacac agaggactac   10860
attcaaacag gtcctgggca gctgtacgcc tactcaaccc ggctgttcac cattgatggc   10920
atcagcatcc catacacatg gaaccacacc gttttctatg atcaggcaca gggaagaatg   10980
```

-continued

```
cctttcttgg ttgaaacact tcatgcatcc tctgtggaat ctgactataa ccagatagaa   11040
gagacactgg gttttaaaat tcatgcttca atatccaaag gagatcgcag taatcagtgc   11100
ccctccgggt ttaccttaga ctcagttgga ccttttttgtg ctgatgagga tgaatgtgca   11160
gcagggaatc cctgctccca tagctgccac aatgccatgg ggacttacta ctgctcctgc   11220
cctaaaggcc tcaccatagc tgcagatgga agaacttgtc aagatattga tgagtgtgct   11280
ttgggtaggc ataccctgcca cgctggtcag gactgtgaca atacgattgg atcttatcgc   11340
tgtgtggtcc gttgtggaag tggctttcga agaacctctg atgggctgag ttgtcaagat   11400
attaatgaat gtcaagaatc cagcccctgt caccagcgct gtttcaatgc cataggaagt   11460
ttccattgtg gatgtgaacc tgggtatcag ctcaaaggca gaaaatgcat ggatgtgaac   11520
gagtgtagac aaaatgtatg cagaccagat cagcactgta agaacacccg tggtggctat   11580
aagtgcattg atctttgtcc aaatggaatg accaaggcag aaaatggaac ctgtattgat   11640
attgatgaat gtaaagatgg gacccatcag tgcagatata accagatatg tgagaataca   11700
agaggcagct atcgttgtgt atgcccaaga ggttatcggt ctcaaggagt tggaagaccc   11760
tgcatggata ttgatgaatg tgaaaataca gatgcctgcc agcatgagtg taagaatacc   11820 tttgaagtt atcagtgcat ctgcccacct ggctatcaac tcacacacaa tggaaagaca   11880
tgccaagata tcgatgaatg tctggagcag aatgtgcact gtggacccaa tcgcatgtgc   11940
ttcaacatga aggaagcta ccagtgcatc gatacaccct gtccacccaa ctaccaacgg   12000
gatcctgttt caggggttctg cctcaagaac tgtccaccca atgatttgga atgtgccttg   12060
agcccatatg ccttggaata caaactcgtc tccctcccat ttggaatagc caccaatcaa   12120
gatttaatcc ggctggttgc atacacacag atggagtga tgcatcccag acaactttc   12180 ctcatggtag atgaggaaca gactgttcct tttgccttga gggatgaaaa cctgaaagga   12240
gtggtgtata caacacgacc actacgagaa gcagagacct accgcatgag ggtccgagcc   12300
tcatcctaca gtgccaatgg gaccattgaa tatcagacca cattcatagt ttatatagct   12360
gtgtccgcct atccatacta a                                             12381
```

<210> SEQ ID NO 4
<211> LENGTH: 4126
<212> TYPE: PRT
<213> ORGANISM: homo sapiens
<220> FEATURE:
<221> NAME/KEY: VARIANT
<222> LOCATION: (1)...(4126)
<223> OTHER INFORMATION: Xaa = Any Amino Acid

<400> SEQUENCE: 4

```
Met Trp Tyr Lys Asp Asn Val Gln Val Thr Glu Ser Ser Thr Ile Gln
 1               5                  10                  15

Thr Val Asn Asn Gly Lys Ile Leu Lys Leu Phe Arg Ala Thr Pro Glu
             20                  25                  30

Asp Ala Gly Arg Tyr Ser Cys Lys Ala Ile Asn Ile Ala Gly Thr Ser
         35                  40                  45

Gln Lys Tyr Phe Asn Ile Asp Val Leu Val Pro Thr Ile Ile Gly
     50                  55                  60

Thr Asn Phe Pro Asn Glu Val Ser Val Val Leu Asn Arg Asp Val Ala
 65                  70                  75                  80

Leu Glu Cys Gln Val Lys Gly Thr Pro Phe Pro Asp Ile His Trp Phe
                 85                  90                  95
```

```
Lys Asp Gly Lys Pro Leu Phe Leu Gly Asp Pro Asn Val Glu Leu Leu
            100                 105                 110

Asp Arg Gly Gln Val Leu His Leu Lys Asn Ala Arg Arg Asn Asp Lys
            115                 120                 125

Gly Arg Tyr Gln Cys Thr Val Ser Asn Ala Ala Gly Lys Gln Ala Lys
            130                 135                 140

Asp Ile Lys Leu Thr Ile Tyr Ile Pro Pro Ser Ile Lys Gly Gly Asn
145                 150                 155                 160

Val Thr Thr Xaa Ile Ser Val Leu Ile Asn Ser Leu Ile Lys Leu Glu
                165                 170                 175

Cys Glu Thr Arg Gly Leu Pro Met Pro Ala Ile Thr Trp Tyr Lys Asp
                180                 185                 190

Gly Gln Pro Ile Met Ser Ser Gln Ala Leu Tyr Ile Asp Lys Gly
            195                 200                 205

Gln Tyr Leu His Ile Pro Arg Ala Gln Val Ser Asp Ser Ala Thr Tyr
            210                 215                 220

Thr Cys His Val Ala Asn Val Ala Gly Thr Ala Glu Lys Ser Phe His
225                 230                 235                 240

Val Asp Val Tyr Val Pro Pro Met Ile Glu Gly Asn Leu Ala Thr Pro
                245                 250                 255

Leu Asn Lys Gln Val Val Ile Ala His Ser Leu Thr Leu Glu Cys Lys
                260                 265                 270

Ala Ala Gly Asn Pro Ser Pro Ile Leu Thr Trp Leu Lys Asp Gly Val
            275                 280                 285

Pro Val Lys Ala Asn Asp Asn Ile Arg Ile Glu Ala Gly Gly Lys Lys
            290                 295                 300

Leu Glu Ile Met Ser Ala Gln Glu Ile Asp Arg Gly Gln Tyr Ile Cys
305                 310                 315                 320

Val Ala Thr Ser Val Ala Gly Glu Lys Glu Ile Lys Tyr Glu Val Asp
                325                 330                 335

Val Leu Val Pro Pro Ala Ile Glu Gly Gly Asp Glu Thr Ser Tyr Phe
            340                 345                 350

Ile Val Met Val Asn Asn Leu Leu Glu Leu Asp Cys His Val Thr Gly
            355                 360                 365

Ser Pro Pro Thr Ile Met Trp Leu Lys Asp Gly Gln Leu Ile Asp
370                 375                 380

Glu Arg Asp Gly Phe Lys Ile Leu Leu Asn Gly Arg Lys Leu Val Ile
385                 390                 395                 400

Ala Gln Ala Gln Val Ser Asn Thr Gly Leu Tyr Arg Cys Met Ala Ala
                405                 410                 415

Asn Thr Ala Gly Asp His Lys Lys Glu Phe Glu Val Thr Val His Val
            420                 425                 430

Pro Pro Thr Ile Lys Ser Ser Gly Leu Ser Glu Arg Val Val Lys
            435                 440                 445

Tyr Lys Pro Val Ala Leu Gln Cys Ile Ala Asn Gly Ile Pro Asn Pro
            450                 455                 460

Ser Ile Thr Trp Leu Lys Asp Asp Gln Pro Val Asn Thr Ala Gln Gly
465                 470                 475                 480

Asn Leu Lys Ile Gln Ser Ser Gly Arg Val Leu Gln Ile Ala Lys Thr
            485                 490                 495

Leu Leu Glu Asp Ala Gly Arg Tyr Thr Cys Val Ala Thr Asn Ala Ala
            500                 505                 510

Gly Glu Thr Gln Gln His Ile Gln Leu His Val His Glu Pro Pro Ser
```

-continued

```
            515                 520                 525
Leu Glu Asp Ala Gly Lys Met Leu Asn Glu Thr Val Leu Val Ser Asn
    530                 535                 540
Pro Val Gln Leu Glu Cys Lys Ala Ala Gly Asn Pro Val Pro Val Ile
545                 550                 555                 560
Thr Trp Tyr Lys Asp Asn Arg Leu Leu Ser Gly Ser Thr Ser Met Thr
                565                 570                 575
Phe Leu Asn Arg Gly Gln Ile Ile Asp Ile Glu Ser Ala Gln Ile Ser
            580                 585                 590
Asp Ala Gly Ile Tyr Lys Cys Val Ala Ile Asn Ser Ala Gly Ala Thr
        595                 600                 605
Glu Leu Phe Tyr Ser Leu Gln Val His Val Ala Pro Ser Ile Ser Gly
    610                 615                 620
Ser Asn Asn Met Val Ala Val Val Asn Asn Pro Val Arg Leu Glu
625                 630                 635                 640
Cys Glu Ala Arg Gly Ile Pro Ala Pro Ser Leu Thr Trp Leu Lys Asp
                645                 650                 655
Gly Ser Pro Val Ser Ser Phe Ser Asn Gly Leu Gln Val Leu Ser Gly
            660                 665                 670
Gly Arg Ile Leu Ala Leu Thr Ser Ala Gln Ile Ser Asp Thr Gly Arg
        675                 680                 685
Tyr Thr Cys Val Ala Val Asn Ala Ala Gly Glu Lys Gln Arg Asp Ile
    690                 695                 700
Asp Leu Arg Val Tyr Val Pro Pro Asn Ile Met Gly Glu Glu Gln Asn
705                 710                 715                 720
Val Ser Val Leu Ile Ser Gln Ala Val Glu Leu Leu Cys Gln Ser Asp
                725                 730                 735
Ala Ile Pro Pro Thr Leu Thr Trp Leu Lys Asp Gly His Pro Leu
            740                 745                 750
Leu Lys Lys Pro Gly Leu Ser Ile Ser Glu Asn Arg Ser Val Leu Lys
        755                 760                 765
Ile Glu Asp Ala Gln Val Gln Asp Thr Gly Arg Tyr Thr Cys Glu Ala
    770                 775                 780
Thr Asn Val Ala Gly Lys Thr Glu Lys Asn Tyr Asn Val Asn Ile Trp
785                 790                 795                 800
Val Pro Pro Asn Ile Gly Gly Ser Asp Glu Leu Thr Gln Leu Thr Val
                805                 810                 815
Ile Glu Gly Asn Leu Ile Ser Leu Leu Cys Glu Ser Ser Gly Ile Pro
            820                 825                 830
Pro Pro Asn Leu Ile Trp Lys Lys Lys Gly Ser Pro Val Leu Thr Asp
        835                 840                 845
Ser Met Gly Arg Xaa Arg Ile Leu Ser Gly Gly Arg Gln Leu Gln Ile
    850                 855                 860
Ser Ile Ala Glu Lys Ser Asp Ala Ala Leu Tyr Ser Cys Val Ala Ser
865                 870                 875                 880
Asn Val Ala Gly Thr Ala Lys Lys Glu Tyr Asn Leu Gln Val Tyr Ile
                885                 890                 895
Arg Pro Thr Ile Thr Asn Ser Gly Ser His Pro Thr Glu Ile Ile Val
            900                 905                 910
Thr Arg Gly Lys Ser Ile Ser Leu Glu Cys Glu Val Gln Gly Ile Pro
        915                 920                 925
Pro Pro Thr Val Thr Trp Met Lys Asp Gly His Pro Leu Ile Lys Ala
    930                 935                 940
```

-continued

```
Lys Gly Val Glu Ile Leu Asp Glu Gly His Ile Leu Gln Leu Lys Asn
945                 950                 955                 960

Ile His Val Ser Asp Thr Gly Arg Tyr Val Cys Val Ala Val Asn Val
                965                 970                 975

Ala Gly Met Thr Asp Lys Lys Tyr Asp Leu Ser Val His Ala Pro Pro
            980                 985                 990

Ser Ile Ile Gly Asn His Arg Ser Pro Glu Asn Ile Ser Val Val Glu
        995                 1000                1005

Lys Asn Ser Val Ser Leu Thr Cys Glu Ala Ser Gly Ile Pro Leu Pro
    1010                1015                1020

Ser Xaa Thr Trp Phe Lys Asp Gly Trp Pro Val Ser Leu Ser Asn Ser
1025                1030                1035                1040

Val Arg Ile Leu Ser Gly Gly Arg Met Leu Arg Leu Met Gln Thr Thr
                1045                1050                1055

Met Glu Asp Ala Gly Gln Tyr Thr Cys Val Val Arg Asn Ala Ala Gly
            1060                1065                1070

Glu Glu Arg Lys Ile Phe Gly Leu Ser Val Leu Val Pro Pro His Ile
        1075                1080                1085

Val Gly Glu Asn Thr Leu Glu Asp Val Lys Val Lys Glu Lys Gln Ser
    1090                1095                1100

Val Thr Leu Thr Cys Glu Val Thr Gly Asn Pro Val Pro Glu Ile Thr
1105                1110                1115                1120

Trp His Lys Asp Gly Gln Pro Leu Gln Glu Asp Glu Ala His Ile
                1125                1130                1135

Ile Ser Gly Gly Arg Phe Leu Gln Ile Thr Asn Val Gln Val Pro His
            1140                1145                1150

Thr Gly Arg Tyr Thr Cys Leu Ala Ser Ser Pro Ala Gly His Lys Ser
        1155                1160                1165

Arg Ser Phe Ser Leu Asn Val Phe Val Ser Pro Thr Ile Ala Gly Val
    1170                1175                1180

Gly Ser Asp Gly Asn Pro Glu Asp Val Thr Val Ile Leu Asn Ser Pro
1185                1190                1195                1200

Thr Ser Leu Val Cys Glu Ala Tyr Ser Tyr Pro Pro Ala Thr Ile Thr
                1205                1210                1215

Trp Phe Lys Asp Gly Thr Pro Leu Glu Ser Asn Arg Asn Ile Arg Ile
            1220                1225                1230

Leu Pro Gly Gly Arg Thr Leu Gln Ile Leu Asn Ala Gln Glu Asp Asn
        1235                1240                1245

Ala Gly Arg Tyr Ser Cys Val Ala Thr Asn Glu Ala Gly Glu Met Ile
    1250                1255                1260

Lys His Tyr Glu Val Lys Val Tyr Ile Pro Pro Ile Ile Asn Lys Gly
1265                1270                1275                1280

Asp Leu Trp Gly Pro Gly Leu Ser Pro Lys Glu Val Lys Ile Lys Val
                1285                1290                1295

Asn Asn Thr Leu Thr Leu Glu Cys Glu Ala Tyr Ala Ile Pro Ser Ala
            1300                1305                1310

Ser Leu Ser Trp Tyr Lys Asp Gly Gln Pro Leu Lys Ser Asp Asp His
        1315                1320                1325

Val Asn Ile Ala Ala Asn Gly His Thr Leu Gln Ile Lys Glu Ala Gln
    1330                1335                1340

Ile Ser Asp Thr Gly Arg Tyr Thr Cys Val Ala Ser Asn Ile Ala Gly
1345                1350                1355                1360
```

-continued

```
Glu Asp Glu Leu Asp Phe Asp Val Asn Ile Gln Val Pro Pro Ser Phe
            1365                1370                1375

Gln Lys Leu Trp Glu Ile Gly Asn Met Leu Asp Thr Gly Arg Asn Gly
        1380                1385                1390

Glu Ala Lys Asp Val Ile Ile Asn Asn Pro Ile Ser Leu Tyr Cys Glu
    1395                1400                1405

Thr Asn Ala Ala Pro Pro Thr Leu Thr Trp Tyr Lys Asp Gly His
1410                1415                1420

Pro Leu Thr Ser Ser Asp Lys Val Leu Ile Leu Pro Gly Gly Arg Val
1425                1430                1435                1440

Leu Gln Ile Pro Arg Ala Lys Val Glu Asp Ala Gly Arg Tyr Thr Cys
                1445                1450                1455

Val Ala Val Asn Glu Ala Gly Glu Asp Ser Leu Gln Tyr Asp Val Arg
            1460                1465                1470

Val Leu Val Pro Pro Ile Ile Lys Gly Ala Asn Ser Asp Leu Pro Glu
        1475                1480                1485

Glu Val Thr Val Leu Val Asn Lys Ser Ala Leu Ile Glu Cys Leu Ser
    1490                1495                1500

Ser Gly Ser Pro Ala Pro Arg Asn Ser Trp Gln Lys Asp Gly Gln Pro
1505                1510                1515                1520

Leu Leu Glu Asp Asp His His Lys Phe Leu Ser Asn Gly Arg Ile Leu
                1525                1530                1535

Gln Ile Leu Asn Thr Gln Ile Thr Asp Ile Gly Arg Tyr Val Cys Val
            1540                1545                1550

Ala Glu Asn Thr Ala Gly Ser Ala Lys Lys Tyr Phe Asn Leu Asn Val
        1555                1560                1565

His Val Pro Pro Ser Val Ile Gly Pro Lys Ser Glu Asn Leu Thr Val
    1570                1575                1580

Val Val Asn Asn Phe Ile Ser Leu Thr Cys Glu Val Ser Gly Phe Pro
1585                1590                1595                1600

Pro Pro Asp Leu Ser Trp Leu Lys Asn Glu Gln Pro Ile Lys Leu Asn
                1605                1610                1615

Thr Asn Thr Leu Ile Val Pro Gly Gly Arg Thr Leu Gln Ile Ile Arg
            1620                1625                1630

Ala Lys Val Ser Asp Gly Gly Glu Tyr Thr Cys Ile Ala Ile Asn Gln
        1635                1640                1645

Ala Gly Glu Ser Lys Lys Lys Phe Ser Leu Thr Val Tyr Val Pro Pro
    1650                1655                1660

Ser Ile Lys Asp His Asp Ser Glu Ser Leu Ser Val Val Asn Val Arg
1665                1670                1675                1680

Glu Gly Thr Ser Val Ser Leu Glu Cys Glu Ser Asn Ala Val Pro Pro
                1685                1690                1695

Pro Val Ile Thr Trp Tyr Lys Asn Gly Arg Met Ile Thr Glu Ser Thr
            1700                1705                1710

His Val Glu Ile Leu Ala Asp Gly Gln Met Leu His Ile Lys Lys Ala
        1715                1720                1725

Glu Val Ser Asp Thr Gly Gln Tyr Val Cys Arg Ala Ile Asn Val Ala
    1730                1735                1740

Gly Arg Asp Asp Lys Asn Phe His Leu Asn Val Tyr Val Pro Pro Ser
1745                1750                1755                1760

Ile Glu Gly Pro Glu Arg Glu Val Ile Val Glu Thr Ile Ser Asn Pro
                1765                1770                1775

Val Thr Leu Thr Cys Asp Ala Thr Gly Ile Pro Pro Pro Thr Ile Ala
```

-continued

```
              1780               1785              1790
Trp Leu Lys Asn His Lys Arg Ile Glu Asn Ser Asp Ser Leu Glu Val
    1795              1800              1805
Arg Ile Leu Ser Gly Gly Ser Lys Leu Gln Ile Ala Arg Ser Gln His
    1810              1815              1820
Ser Asp Ser Gly Asn Tyr Thr Cys Ile Ala Ser Asn Met Glu Gly Lys
1825              1830              1835              1840
Ala Gln Lys Tyr Tyr Phe Leu Ser Ile Gln Val Pro Pro Ser Val Ala
              1845              1850              1855
Gly Ala Glu Ile Pro Ser Asp Val Ser Val Leu Leu Gly Glu Asn Val
              1860              1865              1870
Glu Leu Val Cys Asn Ala Asn Gly Ile Pro Thr Pro Leu Ile Gln Trp
              1875              1880              1885
Leu Lys Asp Gly Lys Pro Ile Ala Ser Gly Glu Thr Glu Arg Ile Arg
              1890              1895              1900
Val Ser Ala Asn Gly Ser Thr Leu Asn Ile Tyr Gly Ala Leu Thr Ser
1905              1910              1915              1920
Asp Thr Gly Lys Tyr Thr Cys Val Ala Thr Asn Pro Ala Gly Glu Glu
              1925              1930              1935
Asp Arg Ile Phe Asn Leu Asn Val Tyr Val Thr Pro Thr Ile Arg Gly
              1940              1945              1950
Asn Lys Asp Glu Ala Glu Lys Leu Met Thr Leu Val Asp Thr Ser Ile
              1955              1960              1965
Asn Ile Glu Cys Arg Ala Thr Gly Thr Pro Pro Pro Gln Ile Asn Trp
              1970              1975              1980
Leu Lys Asn Gly Leu Pro Leu Pro Leu Ser Ser His Ile Arg Leu Leu
1985              1990              1995              2000
Ala Ala Gly Gln Val Ile Arg Ile Val Arg Ala Gln Val Ser Asp Val
              2005              2010              2015
Ala Val Tyr Thr Cys Val Ala Ser Asn Arg Ala Gly Val Asp Asn Lys
              2020              2025              2030
His Tyr Asn Leu Gln Val Phe Ala Pro Pro Asn Met Asp Asn Ser Met
              2035              2040              2045
Gly Thr Glu Glu Ile Thr Val Leu Lys Gly Ser Ser Thr Ser Met Ala
              2050              2055              2060
Cys Ile Thr Asp Gly Thr Pro Ala Pro Ser Met Ala Trp Leu Arg Asp
2065              2070              2075              2080
Gly Gln Pro Leu Gly Leu Asp Ala His Leu Thr Val Ser Thr His Gly
              2085              2090              2095
Met Val Leu Gln Leu Leu Lys Ala Glu Thr Glu Asp Ser Gly Lys Tyr
              2100              2105              2110
Thr Cys Ile Ala Ser Asn Glu Ala Gly Glu Val Ser Lys His Phe Ile
              2115              2120              2125
Leu Lys Val Leu Glu Pro Pro His Ile Asn Gly Ser Glu Glu His Glu
              2130              2135              2140
Glu Ile Ser Val Ile Val Asn Asn Pro Leu Glu Leu Thr Cys Ile Ala
2145              2150              2155              2160
Ser Gly Ile Pro Ala Pro Lys Met Thr Trp Met Lys Asp Gly Arg Pro
              2165              2170              2175
Leu Pro Gln Thr Asp Gln Val Gln Thr Leu Gly Gly Gly Glu Val Leu
              2180              2185              2190
Arg Ile Ser Thr Ala Gln Val Glu Asp Thr Gly Arg Tyr Thr Cys Leu
              2195              2200              2205
```

-continued

```
Ala Ser Ser Pro Ala Gly Asp Asp Lys Glu Tyr Leu Val Arg Val
    2210                2215                2220

His Val Pro Pro Asn Ile Ala Gly Thr Asp Glu Pro Arg Asp Ile Thr
2225                2230                2235                2240

Val Leu Arg Asn Arg Gln Val Thr Leu Glu Cys Lys Ser Asp Ala Val
                2245                2250                2255

Pro Pro Pro Val Ile Thr Trp Leu Arg Asn Gly Glu Arg Leu Gln Ala
            2260                2265                2270

Thr Pro Arg Val Arg Ile Leu Ser Gly Gly Arg Tyr Leu Gln Ile Asn
            2275                2280                2285

Asn Ala Asp Leu Gly Asp Thr Ala Asn Tyr Thr Cys Val Ala Ser Asn
    2290                2295                2300

Ile Ala Gly Lys Thr Thr Arg Glu Phe Ile Leu Thr Val Asn Val Pro
2305                2310                2315                2320

Pro Asn Ile Lys Gly Gly Pro Gln Ser Leu Val Ile Leu Leu Asn Lys
                2325                2330                2335

Ser Thr Val Leu Glu Cys Ile Ala Glu Gly Val Pro Thr Pro Arg Ile
            2340                2345                2350

Thr Trp Arg Lys Asp Gly Ala Val Leu Ala Gly Asn His Ala Arg Tyr
            2355                2360                2365

Ser Ile Leu Glu Asn Gly Phe Leu His Ile Gln Ser Ala His Val Thr
    2370                2375                2380

Asp Thr Gly Arg Tyr Leu Cys Met Ala Thr Asn Ala Ala Gly Thr Asp
2385                2390                2395                2400

Arg Arg Arg Ile Asp Leu Gln Val His Val Pro Pro Ser Ile Ala Pro
                2405                2410                2415

Gly Pro Thr Asn Met Thr Val Ile Val Asn Val Gln Thr Thr Leu Ala
            2420                2425                2430

Cys Glu Ala Thr Gly Ile Pro Lys Pro Ser Ile Asn Trp Arg Lys Asn
            2435                2440                2445

Gly His Leu Leu Asn Val Asp Gln Asn Gln Asn Ser Tyr Arg Leu Leu
    2450                2455                2460

Ser Ser Gly Ser Leu Val Ile Ile Ser Pro Ser Val Asp Asp Thr Ala
2465                2470                2475                2480

Thr Tyr Glu Cys Thr Val Thr Asn Gly Ala Gly Asp Asp Lys Arg Thr
                2485                2490                2495

Val Asp Leu Thr Val Gln Val Pro Pro Ser Ile Ala Asp Glu Pro Thr
            2500                2505                2510

Asp Phe Leu Val Thr Lys His Ala Pro Ala Val Ile Thr Cys Thr Ala
            2515                2520                2525

Ser Gly Val Pro Phe Pro Ser Ile His Trp Thr Lys Asn Gly Ile Arg
    2530                2535                2540

Leu Leu Pro Arg Gly Asp Gly Tyr Arg Ile Leu Ser Ser Gly Ala Ile
2545                2550                2555                2560

Glu Ile Leu Ala Thr Gln Leu Asn His Ala Gly Arg Tyr Thr Cys Val
                2565                2570                2575

Ala Arg Asn Ala Ala Gly Ser Ala His Arg His Val Thr Leu His Val
            2580                2585                2590

His Glu Pro Pro Val Ile Gln Pro Gln Pro Ser Glu Leu His Val Ile
            2595                2600                2605

Leu Asn Asn Pro Ile Leu Leu Pro Cys Glu Ala Thr Gly Thr Pro Ser
    2610                2615                2620
```

-continued

```
Pro Phe Ile Thr Trp Gln Lys Glu Gly Ile Asn Val Asn Thr Ser Gly
2625                2630                2635                2640

Arg Asn His Ala Val Leu Pro Ser Gly Gly Leu Gln Ile Xaa Arg Ala
                2645                2650                2655

Val Arg Glu Asp Ala Gly Thr Tyr Met Cys Val Ala Gln Asn Pro Ala
            2660                2665                2670

Gly Thr Ala Leu Gly Lys Ile Lys Leu Asn Val Gln Val Pro Pro Val
        2675                2680                2685

Ile Ser Pro His Leu Lys Glu Tyr Val Ile Ala Val Asp Lys Pro Ile
    2690                2695                2700

Thr Leu Ser Cys Glu Ala Asp Gly Leu Pro Pro Pro Asp Ile Thr Trp
2705                2710                2715                2720

His Lys Asp Gly Arg Ala Ile Val Glu Ser Ile Arg Gln Arg Val Leu
                2725                2730                2735

Ser Ser Gly Ser Leu Gln Ile Ala Phe Val Gln Pro Gly Asp Ala Gly
            2740                2745                2750

His Tyr Thr Cys Met Ala Ala Asn Val Ala Gly Ser Ser Thr Ser
        2755                2760                2765

Thr Lys Leu Thr Val His Val Pro Pro Arg Ile Arg Ser Thr Glu Gly
    2770                2775                2780

His Tyr Thr Val Asn Glu Asn Ser Gln Ala Ile Leu Pro Cys Val Ala
2785                2790                2795                2800

Asp Gly Ile Pro Thr Pro Ala Ile Asn Trp Lys Lys Asp Asn Val Leu
                2805                2810                2815

Leu Ala Asn Leu Leu Gly Lys Tyr Thr Ala Glu Pro Tyr Gly Glu Leu
            2820                2825                2830

Ile Leu Glu Asn Val Val Leu Glu Asp Ser Gly Phe Tyr Thr Cys Val
        2835                2840                2845

Ala Asn Asn Ala Ala Gly Glu Asp Thr His Thr Val Ser Leu Thr Val
    2850                2855                2860

His Val Leu Pro Thr Phe Thr Glu Leu Pro Gly Asp Val Ser Leu Asn
2865                2870                2875                2880

Lys Gly Glu Gln Leu Arg Leu Ser Cys Lys Ala Thr Gly Ile Pro Leu
                2885                2890                2895

Pro Lys Leu Thr Trp Thr Phe Asn Asn Asn Ile Ile Pro Ala His Phe
            2900                2905                2910

Asp Ser Val Asn Gly His Ser Glu Leu Val Ile Glu Arg Val Ser Lys
        2915                2920                2925

Glu Asp Ser Gly Thr Tyr Val Cys Thr Ala Glu Asn Ser Val Gly Phe
    2930                2935                2940

Val Lys Ala Ile Gly Phe Val Tyr Val Lys Glu Pro Pro Val Phe Lys
2945                2950                2955                2960

Gly Asp Tyr Pro Ser Asn Trp Ile Glu Pro Leu Gly Gly Asn Ala Ile
                2965                2970                2975

Leu Asn Cys Glu Val Lys Gly Asp Pro Thr Pro Thr Ile Gln Trp Asn
            2980                2985                2990

Arg Lys Gly Val Asp Ile Glu Ile Ser His Arg Ile Arg Gln Leu Gly
        2995                3000                3005

Asn Gly Ser Leu Ala Ile Tyr Gly Thr Val Asn Glu Asp Ala Gly Asp
    3010                3015                3020

Tyr Thr Cys Val Ala Thr Asn Glu Ala Gly Val Val Glu Arg Ser Met
3025                3030                3035                3040

Ser Leu Thr Leu Gln Ser Pro Pro Ile Ile Thr Leu Glu Pro Val Glu
```

```
                    3045           3050           3055
Thr Val Ile Asn Ala Gly Gly Lys Ile Ile Leu Asn Cys Gln Ala Thr
            3060           3065           3070
Gly Glu Pro Gln Pro Thr Ile Thr Trp Ser Arg Gln Gly His Ser Ile
            3075           3080           3085
Ser Trp Asp Asp Arg Val Asn Val Leu Ser Asn Asn Ser Leu Tyr Ile
            3090           3095           3100
Ala Asp Ala Gln Lys Glu Asp Thr Ser Glu Phe Glu Cys Val Ala Arg
3105           3110           3115           3120
Asn Leu Met Gly Ser Val Leu Val Arg Val Pro Val Ile Val Gln Val
            3125           3130           3135
His Gly Gly Phe Ser Gln Trp Ser Ala Trp Arg Ala Cys Ser Val Thr
            3140           3145           3150
Cys Gly Lys Gly Ile Gln Lys Arg Ser Arg Leu Cys Asn Gln Pro Leu
            3155           3160           3165
Pro Ala Asn Gly Gly Lys Pro Cys Gln Gly Ser Asp Leu Glu Met Arg
            3170           3175           3180
Asn Cys Gln Asn Lys Pro Cys Pro Val Asp Gly Ser Trp Ser Glu Trp
3185           3190           3195           3200
Ser Leu Trp Glu Glu Cys Thr Arg Ser Cys Gly Arg Gly Asn Gln Thr
            3205           3210           3215
Arg Thr Arg Thr Cys Asn Asn Pro Ser Val Gln His Gly Gly Arg Pro
            3220           3225           3230
Cys Glu Gly Asn Ala Val Glu Ile Ile Met Cys Asn Ile Arg Pro Cys
            3235           3240           3245
Pro Val His Gly Ala Trp Ser Ala Trp Gln Pro Trp Gly Thr Cys Ser
            3250           3255           3260
Glu Ser Cys Gly Lys Gly Thr Gln Thr Arg Ala Arg Leu Cys Asn Asn
3265           3270           3275           3280
Pro Pro Pro Ala Phe Gly Gly Ser Tyr Cys Asp Gly Ala Glu Thr Gln
            3285           3290           3295
Met Gln Val Cys Asn Glu Arg Asn Cys Pro Ile His Gly Lys Trp Ala
            3300           3305           3310
Thr Trp Ala Ser Trp Ser Ala Cys Ser Val Ser Cys Gly Gly Gly Ala
            3315           3320           3325
Arg Gln Arg Thr Arg Gly Cys Ser Asp Pro Val Pro Gln Tyr Gly Gly
            3330           3335           3340
Arg Lys Cys Glu Gly Ser Asp Val Gln Ser Asp Phe Cys Asn Ser Asp
3345           3350           3355           3360
Pro Cys Pro Thr His Gly Asn Trp Ser Pro Trp Ser Gly Trp Gly Thr
            3365           3370           3375
Cys Ser Arg Thr Cys Asn Gly Gly Gln Met Arg Arg Tyr Arg Thr Cys
            3380           3385           3390
Asp Asn Pro Pro Pro Ser Asn Gly Gly Arg Ala Cys Gly Gly Pro Asp
            3395           3400           3405
Ser Gln Ile Gln Arg Cys Asn Thr Asp Met Cys Pro Val Asp Gly Ser
            3410           3415           3420
Trp Gly Ser Trp His Ser Trp Ser Gln Cys Ser Ala Ser Cys Gly Gly
3425           3430           3435           3440
Gly Glu Lys Thr Arg Lys Arg Leu Cys Asp His Pro Val Pro Val Lys
            3445           3450           3455
Gly Gly Arg Pro Cys Pro Gly Asp Thr Thr Gln Val Thr Arg Cys Asn
            3460           3465           3470
```

-continued

```
Val Gln Ala Cys Pro Gly Gly Pro Gln Arg Ala Arg Gly Ser Val Ile
        3475                3480                3485
Gly Asn Ile Asn Asp Val Glu Phe Gly Ile Ala Phe Leu Asn Ala Thr
    3490                3495                3500
Ile Thr Asp Ser Pro Asn Ser Asp Thr Arg Ile Ile Arg Ala Lys Ile
3505                3510                3515                3520
Thr Asn Val Pro Arg Ser Leu Gly Ser Ala Met Arg Lys Ile Val Ser
            3525                3530                3535
Ile Leu Asn Pro Ile Tyr Trp Thr Thr Ala Lys Glu Ile Gly Glu Ala
        3540                3545                3550
Val Asn Gly Phe Thr Leu Thr Asn Ala Val Phe Lys Arg Glu Thr Gln
        3555                3560                3565
Val Glu Phe Ala Thr Gly Glu Ile Leu Gln Met Ser His Ile Ala Arg
        3570                3575                3580
Gly Leu Asp Ser Asp Gly Ser Leu Leu Leu Asp Ile Val Val Ser Gly
3585                3590                3595                3600
Tyr Val Leu Gln Leu Gln Ser Pro Ala Glu Val Thr Val Lys Asp Tyr
            3605                3610                3615
Thr Glu Asp Tyr Ile Gln Thr Gly Pro Gly Gln Leu Tyr Ala Tyr Ser
            3620                3625                3630
Thr Arg Leu Phe Thr Ile Asp Gly Ile Ser Ile Pro Tyr Thr Trp Asn
        3635                3640                3645
His Thr Val Phe Tyr Asp Gln Ala Gln Gly Arg Met Pro Phe Leu Val
        3650                3655                3660
Glu Thr Leu His Ala Ser Ser Val Glu Ser Asp Tyr Asn Gln Ile Glu
3665                3670                3675                3680
Glu Thr Leu Gly Phe Lys Ile His Ala Ser Ile Ser Lys Gly Asp Arg
            3685                3690                3695
Ser Asn Gln Cys Pro Ser Gly Phe Thr Leu Asp Ser Val Gly Pro Phe
            3700                3705                3710
Cys Ala Asp Glu Asp Glu Cys Ala Ala Gly Asn Pro Cys Ser His Ser
            3715                3720                3725
Cys His Asn Ala Met Gly Thr Tyr Tyr Cys Ser Cys Pro Lys Gly Leu
        3730                3735                3740
Thr Ile Ala Ala Asp Gly Arg Thr Cys Gln Asp Ile Asp Glu Cys Ala
3745                3750                3755                3760
Leu Gly Arg His Thr Cys His Ala Gly Gln Asp Cys Asp Asn Thr Ile
            3765                3770                3775
Gly Ser Tyr Arg Cys Val Val Arg Cys Gly Ser Gly Phe Arg Arg Thr
            3780                3785                3790
Ser Asp Gly Leu Ser Cys Gln Asp Ile Asn Glu Cys Gln Glu Ser Ser
            3795                3800                3805
Pro Cys His Gln Arg Cys Phe Asn Ala Ile Gly Ser Phe His Cys Gly
            3810                3815                3820
Cys Glu Pro Gly Tyr Gln Leu Lys Gly Arg Lys Cys Met Asp Val Asn
3825                3830                3835                3840
Glu Cys Arg Gln Asn Val Cys Arg Pro Asp Gln His Cys Lys Asn Thr
            3845                3850                3855
Arg Gly Gly Tyr Lys Cys Ile Asp Leu Cys Pro Asn Gly Met Thr Lys
            3860                3865                3870
Ala Glu Asn Gly Thr Cys Ile Asp Ile Asp Glu Cys Lys Asp Gly Thr
            3875                3880                3885
```

```
His Gln Cys Arg Tyr Asn Gln Ile Cys Glu Asn Thr Arg Gly Ser Tyr
    3890                3895                3900
Arg Cys Val Cys Pro Arg Gly Tyr Arg Ser Gln Gly Val Gly Arg Pro
3905            3910                3915                    3920
Cys Met Asp Ile Asp Glu Cys Glu Asn Thr Asp Ala Cys Gln His Glu
            3925            3930                    3935
Cys Lys Asn Thr Phe Gly Ser Tyr Gln Cys Ile Cys Pro Pro Gly Tyr
            3940                3945                3950
Gln Leu Thr His Asn Gly Lys Thr Cys Gln Asp Ile Asp Glu Cys Leu
            3955            3960                3965
Glu Gln Asn Val His Cys Gly Pro Asn Arg Met Cys Phe Asn Met Arg
            3970            3975                3980
Gly Ser Tyr Gln Cys Ile Asp Thr Pro Cys Pro Pro Asn Tyr Gln Arg
3985                3990                3995                4000
Asp Pro Val Ser Gly Phe Cys Leu Lys Asn Cys Pro Pro Asn Asp Leu
                4005            4010                4015
Glu Cys Ala Leu Ser Pro Tyr Ala Leu Glu Tyr Lys Leu Val Ser Leu
            4020            4025                4030
Pro Phe Gly Ile Ala Thr Asn Gln Asp Leu Ile Arg Leu Val Ala Tyr
            4035            4040                4045
Thr Gln Asp Gly Val Met His Pro Arg Thr Thr Phe Leu Met Val Asp
            4050            4055                4060
Glu Glu Gln Thr Val Pro Phe Ala Leu Arg Asp Glu Asn Leu Lys Gly
4065                4070            4075                    4080
Val Val Tyr Thr Thr Arg Pro Leu Arg Glu Ala Glu Thr Tyr Arg Met
            4085            4090                4095
Arg Val Arg Ala Ser Ser Tyr Ser Ala Asn Gly Thr Ile Glu Tyr Gln
            4100            4105                4110
Thr Thr Phe Ile Val Tyr Ile Ala Val Ser Ala Tyr Pro Tyr
            4115            4120            4125
```